United States Patent
Frasier et al.

(10) Patent No.: US 10,022,245 B2
(45) Date of Patent: Jul. 17, 2018

(54) POLYAXIAL ARTICULATING INSTRUMENT

(71) Applicant: DePuy Synthes Products, Inc., Raynham, MA (US)

(72) Inventors: William Frasier, New Bedford, MA (US); Michael J O'Neil, West Barnstable, MA (US); Hassan Serhan, South Easton, MA (US); Henri Defossez, Neuchatel (CH); Thibault Chandanson, Villers le Lac (FR)

(73) Assignee: DePuy Synthes Products, Inc., Raynham, MA (US)

( * ) Notice: Subject to any disclaimer, the term of this patent is extended or adjusted under 35 U.S.C. 154(b) by 153 days.

(21) Appl. No.: 13/744,789

(22) Filed: Jan. 18, 2013

(65) Prior Publication Data

US 2014/0172105 A1    Jun. 19, 2014

Related U.S. Application Data

(60) Provisional application No. 61/738,078, filed on Dec. 17, 2012.

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/442* (2013.01); *A61F 2/4465* (2013.01); *A61F 2/4684* (2013.01); *A61F 2002/30542* (2013.01); *A61F 2002/30777* (2013.01); *A61F 2002/30779* (2013.01); *A61F 2002/30785* (2013.01); *A61F 2002/30787* (2013.01);
(Continued)

(58) Field of Classification Search
CPC ........ A61F 2/44; A61F 2/4425; A61F 2/4611; A61F 2002/0072; A61F 2002/4625; A61F 2002/4627; A61F 2002/4628
USPC ................................ 623/17.11–17.16; 606/99
See application file for complete search history.

(56) References Cited

U.S. PATENT DOCUMENTS

| | | |
|---|---|---|
| 3,426,364 A | 2/1969 | Lumb et al. |
| 3,867,728 A | 2/1975 | Stubstad et al. |

(Continued)

FOREIGN PATENT DOCUMENTS

| | | |
|---|---|---|
| CA | 534357 | 12/1956 |
| DE | 19710392 | 7/1999 |

(Continued)

OTHER PUBLICATIONS

Vandorpe, "Biodegradable Polyphosphazenes for Biomedical Applications"; *Handbook of Biodegradable Polymers*; 1997; pp. 161-182; Hardwood Academic Press.

(Continued)

*Primary Examiner* — Eduardo C Robert
*Assistant Examiner* — Michelle C. Eckman

(57) ABSTRACT

A polyaxial instrument suitable for preparing the intervertebral disc space of a patient through an anterior, posterior, transforaminal or anterolateral approach. The trial can be partially inserted into a disc space and then its angle adjusted to ease its further insertion into the disc space. The trial work tip can be interchangeable with the working tip of another type of instrument such as a curette, a rasp, a spreader, a shaver, a cobb elevator, a penfield, a woodson, a chisel and an osteotome.

44 Claims, 25 Drawing Sheets

(52) U.S. Cl.
CPC .......... A61F 2002/4475 (2013.01); A61F 2002/4628 (2013.01); A61F 2002/4629 (2013.01)

(56) References Cited

U.S. PATENT DOCUMENTS

| | | |
|---|---|---|
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,298,993 A | 11/1981 | Kovaleva et al. |
| 4,349,921 A | 9/1982 | Kuntz |
| 4,394,370 A | 7/1983 | Jefferies |
| 4,450,591 A | 5/1984 | Rappaport |
| 4,454,374 A | 6/1984 | Pollack |
| 4,538,612 A | 9/1985 | Patrick, Jr. |
| 4,545,374 A | 10/1985 | Jacobson |
| 4,599,086 A | 7/1986 | Doty |
| 4,627,853 A | 9/1986 | Campbell et al. |
| 4,714,469 A | 12/1987 | Kenna |
| 4,781,721 A | 1/1988 | Grundei |
| 4,743,256 A | 10/1988 | Brantigan |
| 4,834,757 A | 5/1989 | Brantigan |
| 4,878,915 A | 7/1989 | Brantigan |
| 4,829,152 A | 9/1989 | Rostoker et al. |
| 4,863,476 A | 9/1989 | Shepperd |
| 4,872,452 A | 10/1989 | Alexson |
| 4,877,020 A | 10/1989 | Vich |
| 4,904,261 A | 2/1990 | Dove et al. |
| 4,911,718 A | 3/1990 | Lee |
| 4,917,704 A | 4/1990 | Frey et al. |
| 4,927,425 A | 5/1990 | Lozier |
| 4,941,481 A | 7/1990 | Wagenknecht |
| 4,955,908 A | 11/1990 | Frey et al. |
| 4,995,200 A | 2/1991 | Eberhart |
| 5,006,121 A | 4/1991 | Hafeli |
| 4,997,432 A | 5/1991 | Keller |
| 5,019,082 A | 5/1991 | Frey |
| 5,006,120 A | 9/1991 | Carter |
| 5,047,058 A | 9/1991 | Roberts et al. |
| 5,116,374 A | 5/1992 | Stone |
| 5,123,926 A | 6/1992 | Pisharodi |
| 5,133,719 A | 7/1992 | Winston |
| 5,163,939 A | 11/1992 | Winston |
| 5,169,402 A | 12/1992 | Elloy |
| 5,171,240 A | 12/1992 | Hanwong |
| 5,171,278 A | 12/1992 | Pisharodi |
| 5,171,281 A | 12/1992 | Parsons |
| 5,258,031 A | 2/1993 | Salib et al. |
| 5,190,549 A | 3/1993 | Miller |
| 5,192,327 A | 3/1993 | Brantigan |
| 5,201,736 A | 4/1993 | Strauss |
| 5,217,475 A | 6/1993 | Kuber |
| 5,250,061 A | 10/1993 | Michelson |
| 5,282,861 A | 1/1994 | Kaplan |
| 5,298,254 A | 3/1994 | Prewett et al. |
| 5,306,308 A | 4/1994 | Gross et al. |
| 5,306,309 A | 4/1994 | Wagner et al. |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,397,364 A | 3/1995 | Kozak et al. |
| 5,425,772 A | 6/1995 | Brantigan |
| 5,443,514 A | 8/1995 | Steffee |
| 5,443,515 A | 8/1995 | Cohen et al. |
| 5,454,815 A | 10/1995 | Geisser |
| 5,454,827 A | 10/1995 | Aust |
| 5,431,658 A | 11/1995 | Moskovich |
| 5,464,929 A | 11/1995 | Bezwada |
| 5,476,466 A | 12/1995 | Barrette |
| 5,484,437 A | 1/1996 | Michelson |
| 5,522,899 A | 6/1996 | Michelson |
| 5,540,693 A | 7/1996 | Fisher |
| 5,545,229 A | 8/1996 | Parsons |
| 5,550,172 A | 8/1996 | Regula et al. |
| 5,554,191 A | 9/1996 | Lahille |
| 5,556,431 A | 9/1996 | Buttner-Janz |
| 5,595,751 A | 1/1997 | Bezwada |
| 5,597,579 A | 1/1997 | Bezwada |
| 5,601,561 A | 2/1997 | Terry |
| 5,607,687 A | 3/1997 | Bezwada |
| 5,618,552 A | 4/1997 | Bezwada |
| 5,620,448 A | 4/1997 | Puddu |
| 5,620,698 A | 4/1997 | Bezwada |
| 5,683,463 A | 4/1997 | Godefroy et al. |
| 5,645,850 A | 7/1997 | Bezwada |
| 5,648,088 A | 7/1997 | Bezwada |
| 5,674,296 A | 7/1997 | Bryan et al. |
| 5,645,596 A | 8/1997 | Kim et al. |
| 5,658,335 A | 8/1997 | Allen |
| 5,658,336 A | 8/1997 | Pisharodi |
| 5,665,122 A | 9/1997 | Kambin |
| 5,669,909 A | 9/1997 | Zdeblick et al. |
| 5,609,635 A | 11/1997 | Michelson |
| 5,693,100 A | 12/1997 | Pisharodi |
| 5,698,213 A | 12/1997 | Jamiolkowski |
| 5,700,583 A | 12/1997 | Jamiolkowski |
| 5,702,449 A | 12/1997 | McKay |
| 5,702,463 A | 12/1997 | Pothier |
| 5,707,371 A | 1/1998 | Metz Stavenhagen |
| 5,725,531 A | 3/1998 | Shapiro |
| 5,728,159 A | 3/1998 | Stroever et al. |
| 5,755,798 A | 5/1998 | Papavero et al. |
| 5,766,251 A | 6/1998 | Koshino |
| 5,766,252 A | 6/1998 | Henry et al. |
| 5,772,661 A | 6/1998 | Michelson |
| 5,782,830 A | 7/1998 | Farris |
| 5,782,919 A | 7/1998 | Zdeblick et al. |
| 5,836,948 A | 11/1998 | Zucherman et al. |
| 5,857,995 A | 1/1999 | Thomas |
| 5,859,150 A | 1/1999 | Jamiolkowski |
| 5,860,973 A | 1/1999 | Michelson |
| 5,865,845 A | 2/1999 | Thalgott |
| 5,865,848 A | 2/1999 | Baker |
| 5,888,222 A | 3/1999 | Coates |
| 5,888,223 A | 3/1999 | Bray, Jr. |
| 5,893,890 A | 4/1999 | Pisharodi |
| 5,906,616 A | 5/1999 | Pavlov et al. |
| 5,916,228 A | 6/1999 | Ripich |
| 5,925,056 A | 7/1999 | Thomas |
| 5,968,098 A | 10/1999 | Winslow |
| 5,976,187 A | 11/1999 | Richelsoph |
| 5,980,522 A | 11/1999 | Koros |
| 5,989,289 A | 11/1999 | Coates |
| 5,964,807 A | 12/1999 | Gan et al. |
| 6,001,099 A | 12/1999 | Huebner |
| 6,008,433 A | 12/1999 | Stone |
| 6,039,761 A | 3/2000 | Li |
| 6,039,762 A | 3/2000 | McKay |
| 6,045,579 A | 4/2000 | Hochshuler et al. |
| 6,053,922 A | 4/2000 | Krause |
| 6,056,763 A | 5/2000 | Parsons |
| 6,066,174 A | 5/2000 | Farris |
| 6,066,175 A | 5/2000 | Henderson |
| 6,080,158 A | 6/2000 | Lin |
| 6,099,531 A | 8/2000 | Bonutti |
| 6,106,557 A | 8/2000 | Robioneck |
| 6,120,508 A | 9/2000 | Grunig |
| 6,126,689 A | 10/2000 | Brett |
| 6,139,558 A | 10/2000 | Wagner |
| 6,086,593 A | 11/2000 | Bonutti |
| 6,143,032 A | 11/2000 | Schäfer |
| 6,146,421 A | 11/2000 | Gordon et al. |
| 6,159,215 A | 12/2000 | Urbahns |
| 6,174,311 B1 | 1/2001 | Branch |
| 6,176,882 B1 | 1/2001 | Biedermann |
| 6,206,922 B1 | 3/2001 | Zdeblick et al. |
| 6,231,610 B1 | 5/2001 | Geisler |
| 6,235,059 B1 | 5/2001 | Benezech et al. |
| 6,241,733 B1 | 6/2001 | Nicholson |
| 6,245,108 B1 | 6/2001 | Biscup |

(56) References Cited

U.S. PATENT DOCUMENTS

| | | | |
|---|---|---|---|
| 6,251,140 | B1 | 6/2001 | Marino |
| 6,258,093 | B1 | 7/2001 | Edwards |
| 6,296,644 | B1 | 10/2001 | Saurat |
| 6,309,421 | B1 | 10/2001 | Pisharodi |
| D450,676 | S | 11/2001 | Huttner |
| 6,319,257 | B1 | 11/2001 | Carignan |
| 6,332,894 | B1 | 12/2001 | Stalcup et al. |
| 6,342,074 | B1 | 1/2002 | Simpson |
| 6,364,880 | B1 | 2/2002 | Michelson |
| 6,443,987 | B1 | 3/2002 | Bryan |
| 6,371,988 | B1 | 4/2002 | Pafford |
| 6,387,130 | B1 | 5/2002 | Stone |
| 6,398,793 | B1 | 6/2002 | McGuire |
| 6,409,766 | B1 | 6/2002 | Brett |
| 6,413,278 | B1 | 7/2002 | Marchosky |
| 6,423,095 | B1 | 7/2002 | Van Hoeck |
| 6,425,920 | B1 | 7/2002 | Hamada |
| 6,428,544 | B1 | 8/2002 | Ralph |
| 6,432,106 | B1 | 8/2002 | Fraser |
| 6,436,101 | B1 | 8/2002 | Hamada |
| 6,447,518 | B1 | 9/2002 | Krause |
| 6,447,544 | B1 | 10/2002 | Michelson |
| 6,482,233 | B1 | 11/2002 | Aebi et al. |
| 6,511,509 | B1 | 1/2003 | Ford et al. |
| 6,579,318 | B2 | 6/2003 | Varga |
| 6,582,432 | B1 | 6/2003 | Michelson |
| 6,595,998 | B2 | 7/2003 | Johnson et al. |
| 6,599,294 | B2 | 7/2003 | Fuss |
| 6,605,089 | B1 | 8/2003 | Michelson |
| 6,610,066 | B2 | 8/2003 | Dinger |
| 6,610,089 | B1 | 8/2003 | Liu |
| 6,635,060 | B2 | 10/2003 | Hanson |
| RE38,335 | E | 11/2003 | Aust |
| 6,641,582 | B1 | 11/2003 | Hanson |
| 6,648,915 | B2 | 11/2003 | Sazy |
| 6,660,004 | B2 | 12/2003 | Barker |
| 6,676,703 | B2 | 1/2004 | Biscup |
| 6,699,288 | B2 | 3/2004 | Moret |
| 6,719,794 | B2 | 4/2004 | Gerber |
| 6,733,535 | B2 | 5/2004 | Michelson |
| 6,746,484 | B1 | 6/2004 | Liu |
| 6,755,837 | B2 | 6/2004 | Ebner |
| 6,764,491 | B2 | 7/2004 | Frey |
| 6,767,366 | B2 | 7/2004 | Lee |
| 6,830,570 | B1 | 12/2004 | Frey |
| 6,835,206 | B2 | 12/2004 | Jackson |
| 6,835,208 | B2 | 12/2004 | Marchosky |
| 6,840,941 | B2 * | 1/2005 | Rogers et al. ................. 606/79 |
| 6,852,127 | B2 | 2/2005 | Varga |
| 6,878,167 | B2 | 4/2005 | Ferree |
| 6,949,108 | B2 | 9/2005 | Holmes |
| 6,966,912 | B2 | 11/2005 | Michelson |
| 6,974,480 | B2 | 12/2005 | Messerli |
| 7,018,415 | B1 | 3/2006 | McKay |
| 7,048,762 | B1 | 5/2006 | Sander |
| 7,048,765 | B1 | 5/2006 | Grooms |
| 7,060,073 | B2 | 6/2006 | Frey |
| 7,060,096 | B1 | 6/2006 | Schopf |
| 7,066,961 | B2 | 6/2006 | Michelson |
| 7,070,598 | B2 | 7/2006 | Lim |
| 7,087,055 | B2 | 8/2006 | Lim |
| 7,105,024 | B2 | 9/2006 | Richelsoph |
| 7,112,224 | B2 | 9/2006 | Liu |
| 7,115,128 | B2 | 10/2006 | Michelson |
| 7,115,132 | B2 | 10/2006 | Errico |
| 7,125,424 | B2 | 10/2006 | Banick |
| 7,169,182 | B2 | 1/2007 | Errico |
| 7,169,183 | B2 | 1/2007 | Liu |
| 7,192,447 | B2 | 3/2007 | Rhoda |
| 7,223,292 | B2 | 5/2007 | Messerli |
| 7,226,482 | B2 | 6/2007 | Messerli |
| 7,226,483 | B2 | 6/2007 | Gerber |
| 7,229,477 | B2 | 6/2007 | Biscup |
| 7,235,081 | B2 | 6/2007 | Errico |
| 7,235,082 | B2 | 6/2007 | Bartish |
| 7,291,173 | B2 | 11/2007 | Richelsoph |
| 7,311,734 | B2 | 12/2007 | Van Hoeck |
| 7,320,688 | B2 | 1/2008 | Foley |
| 7,326,248 | B2 | 2/2008 | Michelson |
| 7,331,996 | B2 | 2/2008 | Sato |
| 7,351,262 | B2 | 4/2008 | Bindseil |
| 7,361,193 | B2 | 4/2008 | Frey |
| 7,404,795 | B2 | 7/2008 | Ralph |
| 7,465,305 | B2 | 12/2008 | Liu |
| 7,470,273 | B2 * | 12/2008 | Dougherty-Shah ......... 606/86 A |
| 7,473,268 | B2 | 1/2009 | Zucherman |
| 7,481,812 | B2 | 1/2009 | Frey |
| 7,491,237 | B2 | 2/2009 | Randall |
| 7,500,991 | B2 | 3/2009 | Bartish, Jr. |
| 7,503,920 | B2 | 3/2009 | Siegal |
| 7,572,279 | B2 | 8/2009 | Jackson |
| 7,575,580 | B2 | 8/2009 | Lim |
| 7,578,820 | B2 | 8/2009 | Moore |
| 7,601,173 | B2 | 10/2009 | Messerli |
| 7,608,080 | B2 | 10/2009 | Shipp |
| 7,618,458 | B2 | 11/2009 | Biedermann |
| 7,625,377 | B2 | 12/2009 | Veldhuizen |
| 7,625,394 | B2 | 12/2009 | Molz, IV |
| 7,655,010 | B2 | 2/2010 | Serhan et al. |
| 7,655,045 | B2 | 2/2010 | Richelsoph |
| 7,666,186 | B2 | 2/2010 | Harp |
| 7,666,226 | B2 | 2/2010 | Schaller |
| 7,670,374 | B2 | 3/2010 | Schaller |
| 7,674,265 | B2 | 3/2010 | Smith |
| 7,682,400 | B2 | 3/2010 | Zwirkoski |
| 7,703,727 | B2 | 4/2010 | Selness |
| 7,704,280 | B2 | 4/2010 | Lechmann |
| 7,731,751 | B2 | 6/2010 | Butler |
| 7,763,028 | B2 | 7/2010 | Lim |
| 7,771,473 | B2 | 8/2010 | Thramann |
| 7,785,368 | B2 | 8/2010 | Schaller |
| 7,799,081 | B2 | 9/2010 | McKinley |
| 7,803,161 | B2 | 9/2010 | Foley |
| 7,806,932 | B2 | 10/2010 | Webb |
| 7,811,292 | B2 | 10/2010 | Lo |
| 7,828,849 | B2 | 11/2010 | Lim |
| 7,832,409 | B2 | 11/2010 | Richelsoph |
| 7,837,734 | B2 | 11/2010 | Zucherman |
| 7,850,733 | B2 | 12/2010 | Baynham |
| 7,875,080 | B2 | 1/2011 | Puno |
| 7,901,458 | B2 | 3/2011 | DeRidder |
| 7,918,874 | B2 | 4/2011 | Siegal |
| 7,922,719 | B2 | 4/2011 | Ralph |
| 7,935,124 | B2 | 5/2011 | Frey |
| 7,935,148 | B2 | 5/2011 | Edie |
| 7,938,857 | B2 | 5/2011 | Garcia-Bengochea |
| 7,942,903 | B2 | 5/2011 | Moskowitz |
| 7,959,675 | B2 | 6/2011 | Gately |
| 7,963,967 | B1 | 6/2011 | Woods |
| 7,967,863 | B2 | 6/2011 | Frey |
| 7,976,566 | B2 | 7/2011 | Michelson |
| 7,981,156 | B2 | 7/2011 | Pafford |
| 7,988,695 | B2 | 8/2011 | Dye |
| 7,988,699 | B2 | 8/2011 | Martz |
| 7,993,347 | B1 | 8/2011 | Michelson |
| 7,998,209 | B2 | 8/2011 | Branch |
| 7,998,215 | B2 | 8/2011 | Frey |
| 8,007,535 | B2 | 8/2011 | Hudgins |
| 8,012,212 | B2 | 9/2011 | Link |
| 8,021,430 | B2 | 9/2011 | Michelson |
| 8,025,697 | B2 | 9/2011 | McClellan, III |
| 8,034,110 | B2 | 10/2011 | Garner et al. |
| 8,038,703 | B2 | 10/2011 | Dobak, III |
| 8,043,293 | B2 | 10/2011 | Warnick |
| 8,048,159 | B2 | 11/2011 | Ralph |
| 8,057,544 | B2 | 11/2011 | Schaller |
| 8,066,705 | B2 | 11/2011 | Michelson |
| 8,075,622 | B2 | 12/2011 | Van Hoeck |
| 8,092,539 | B2 | 1/2012 | Ralph |
| 8,092,568 | B2 | 1/2012 | Konomi |
| 8,105,382 | B2 | 1/2012 | Olmos |
| 8,128,700 | B2 | 3/2012 | Delurio |
| 8,206,423 | B2 | 6/2012 | Siegal |
| 8,216,317 | B2 * | 7/2012 | Thibodeau ................. 623/17.16 |

(56) References Cited

U.S. PATENT DOCUMENTS

| | | |
|---|---|---|
| 8,231,675 B2 | 7/2012 | Rhoda |
| 8,241,364 B2 * | 8/2012 | Hansell et al. ............ 623/17.16 |
| 8,262,666 B2 | 9/2012 | Baynham |
| 8,267,939 B2 | 9/2012 | Cipoletti |
| 8,292,959 B2 | 10/2012 | Webb |
| 8,343,193 B2 | 1/2013 | Johnson et al. |
| 8,343,219 B2 | 1/2013 | Allain |
| 8,343,222 B2 | 1/2013 | Cope |
| 8,366,777 B2 | 2/2013 | Matthis |
| 8,372,084 B2 | 2/2013 | Pernsteiner |
| 8,382,842 B2 | 2/2013 | Greenhalgh et al. |
| 8,403,990 B2 | 3/2013 | Dryer et al. |
| 8,409,292 B2 | 4/2013 | Michelson |
| 8,435,300 B2 | 5/2013 | Messerli |
| 8,444,696 B2 | 5/2013 | Michelson |
| 8,454,617 B2 | 6/2013 | Schaller et al. |
| 8,480,745 B2 | 7/2013 | Liu |
| 8,491,654 B2 | 7/2013 | Frey |
| 8,506,629 B2 | 8/2013 | Weiland |
| 8,579,981 B2 | 11/2013 | Lim |
| 8,597,356 B2 | 12/2013 | Rhoda |
| 8,628,577 B1 | 1/2014 | Jimenez |
| 8,663,331 B2 | 3/2014 | McClellan, III |
| 8,690,949 B2 | 4/2014 | Messerli |
| 8,734,447 B1 | 5/2014 | Michaelson |
| 8,758,344 B2 | 6/2014 | Michelson |
| 8,758,358 B2 | 6/2014 | Errico |
| 8,845,733 B2 | 9/2014 | O'Neil |
| 8,845,734 B2 | 9/2014 | O'Neil |
| 8,858,564 B2 | 10/2014 | Errico |
| 8,858,638 B2 | 10/2014 | Michelson |
| 8,920,506 B2 | 12/2014 | McGuckin, Jr. |
| 8,926,704 B2 | 1/2015 | Glerum et al. |
| 8,940,050 B2 | 1/2015 | Laurence |
| 8,961,609 B2 | 2/2015 | Schaller |
| 8,968,408 B2 | 3/2015 | Schaller et al. |
| 8,986,389 B2 | 3/2015 | Lim |
| 9,023,109 B2 | 5/2015 | Weiland |
| 9,101,488 B2 | 8/2015 | Malandain |
| 9,101,492 B2 | 8/2015 | Mangione |
| 9,028,553 B2 | 12/2015 | Lindenmann et al. |
| 9,332,750 B2 | 5/2016 | Mills |
| 9,358,133 B2 | 6/2016 | Lindenmann et al. |
| 2002/0065560 A1 | 5/2002 | Varga |
| 2002/0138078 A1 | 9/2002 | Chappuis |
| 2002/0138146 A1 | 9/2002 | Jackson |
| 2002/0143399 A1 | 10/2002 | Sutcliffe |
| 2002/0165550 A1 | 11/2002 | Frey |
| 2002/0183758 A1 | 12/2002 | Middleton |
| 2002/0193880 A1 | 12/2002 | Fraser |
| 2003/0023306 A1 | 1/2003 | Liu |
| 2003/0028251 A1 | 2/2003 | Mathews |
| 2003/0060886 A1 | 3/2003 | Van Hoeck |
| 2003/0083747 A1 | 5/2003 | Winterbottom |
| 2003/0135275 A1 | 7/2003 | Garcia |
| 2003/0139812 A1 | 7/2003 | Garcia et al. |
| 2003/0139813 A1 | 7/2003 | Messerli |
| 2003/0191531 A1 | 10/2003 | Berry |
| 2003/0199881 A1 | 10/2003 | Bonutti |
| 2004/0002761 A1 | 1/2004 | Rogers et al. |
| 2004/0019356 A1 | 1/2004 | Fraser |
| 2004/0030387 A1 | 2/2004 | Landry |
| 2004/0059337 A1 | 3/2004 | Hanson |
| 2004/0059420 A1 | 3/2004 | Michelson |
| 2004/0068269 A1 | 4/2004 | Bonati |
| 2004/0083000 A1 | 4/2004 | Keller |
| 2004/0087947 A1 | 5/2004 | Lim et al. |
| 2004/0102784 A1 | 5/2004 | Pasquet |
| 2004/0102846 A1 | 5/2004 | Keller |
| 2004/0106996 A1 | 6/2004 | Liu |
| 2004/0127990 A1 | 7/2004 | Bartish |
| 2004/0147129 A1 | 7/2004 | Rolfson |
| 2004/0153065 A1 | 8/2004 | Lim |
| 2004/0186574 A1 | 9/2004 | Varga |
| 2004/0204714 A1 | 10/2004 | Liu |
| 2004/0210308 A1 | 10/2004 | Carter |
| 2004/0220668 A1 | 11/2004 | Eisermann |
| 2004/0230306 A1 | 11/2004 | Hoeck |
| 2005/0038431 A1 * | 2/2005 | Bartish et al. ................ 606/61 |
| 2005/0096745 A1 * | 5/2005 | Andre et al. ............. 623/17.11 |
| 2005/0107878 A1 | 5/2005 | Conchy |
| 2005/0119752 A1 | 6/2005 | Williams et al. |
| 2005/0149034 A1 | 7/2005 | Assell |
| 2005/0165420 A1 | 7/2005 | Cha |
| 2005/0165484 A1 | 7/2005 | Ferree |
| 2005/0165612 A1 | 7/2005 | Rysselberghe |
| 2005/0171541 A1 | 8/2005 | Boehm |
| 2005/0177173 A1 | 8/2005 | Aebi |
| 2005/0240193 A1 | 10/2005 | Layne |
| 2006/0036244 A1 | 2/2006 | Spitler |
| 2006/0058807 A1 | 3/2006 | Landry |
| 2006/0064101 A1 | 3/2006 | Arramon |
| 2006/0064102 A1 | 3/2006 | Ebner |
| 2006/0069436 A1 | 3/2006 | Sutton |
| 2006/0074429 A1 | 4/2006 | Ralph |
| 2006/0100622 A1 | 5/2006 | Jackson |
| 2006/0100705 A1 | 5/2006 | Puno |
| 2006/0106460 A1 | 5/2006 | Messerli |
| 2006/0111715 A1 | 5/2006 | Jackson |
| 2006/0111728 A1 * | 5/2006 | Abdou ............ 606/86 |
| 2006/0116767 A1 | 6/2006 | Magerl |
| 2006/0122701 A1 | 6/2006 | Kiester |
| 2006/0129244 A1 | 6/2006 | Ensign |
| 2006/0142858 A1 | 6/2006 | Colleran |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt |
| 2006/0229724 A1 | 10/2006 | Lechmann |
| 2006/0235426 A1 | 10/2006 | Lim |
| 2006/0253120 A1 * | 11/2006 | Anderson et al. ............. 606/86 |
| 2006/0254784 A1 | 11/2006 | Hartmann et al. |
| 2006/0265077 A1 | 11/2006 | Zwirkoski |
| 2006/0293753 A1 | 12/2006 | Thramann |
| 2007/0010885 A1 | 1/2007 | Liu |
| 2007/0010886 A1 | 1/2007 | Banick |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 * | 4/2007 | Gerbec et al. ............ 623/17.11 |
| 2007/0093901 A1 | 4/2007 | Grotz et al. |
| 2007/0118220 A1 | 5/2007 | Liu |
| 2007/0142843 A1 * | 6/2007 | Dye ................ 606/99 |
| 2007/0162132 A1 | 7/2007 | Messerli |
| 2007/0162138 A1 | 7/2007 | Heinz |
| 2007/0208343 A1 | 9/2007 | Magerl |
| 2007/0213737 A1 * | 9/2007 | Schermerhorn et al. ....... 606/86 |
| 2007/0213826 A1 * | 9/2007 | Smith et al. ............. 623/17.11 |
| 2007/0225726 A1 * | 9/2007 | Dye et al. ........ 606/99 |
| 2007/0225808 A1 | 9/2007 | Warnick |
| 2007/0225815 A1 | 9/2007 | Keith |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham |
| 2007/0282441 A1 | 12/2007 | Stream |
| 2008/0009880 A1 | 1/2008 | Warnick |
| 2008/0015701 A1 | 1/2008 | Garcia |
| 2008/0027544 A1 * | 1/2008 | Melkent ............. 623/17.11 |
| 2008/0027550 A1 | 1/2008 | Link |
| 2008/0045966 A1 | 2/2008 | Buttermann |
| 2008/0051890 A1 | 2/2008 | Waugh |
| 2008/0058933 A1 | 3/2008 | Garner |
| 2008/0065082 A1 | 3/2008 | Chang |
| 2008/0077150 A1 | 3/2008 | Nguyen |
| 2008/0077153 A1 * | 3/2008 | Pernsteiner ........... A61F 2/4425 606/99 |
| 2008/0077241 A1 * | 3/2008 | Nguyen ............. A61B 17/1659 623/17.11 |
| 2008/0077247 A1 | 3/2008 | Murillo |
| 2008/0082173 A1 | 4/2008 | Delurio |
| 2008/0091211 A1 * | 4/2008 | Gately ............. 606/99 |
| 2008/0097454 A1 | 4/2008 | DeRidder |

(56) References Cited

U.S. PATENT DOCUMENTS

| | | | |
|---|---|---|---|
| 2008/0108990 A1 | 5/2008 | Mitchell | |
| 2008/0109083 A1 | 5/2008 | Van Hoeck | |
| 2008/0119935 A1* | 5/2008 | Alvarez | 623/17.16 |
| 2008/0125865 A1 | 5/2008 | Abdelgany | |
| 2008/0133012 A1 | 6/2008 | McGuckin | |
| 2008/0140085 A1* | 6/2008 | Gately | A61F 2/4465 606/99 |
| 2008/0154379 A1 | 6/2008 | Steiner | |
| 2008/0172128 A1 | 7/2008 | Perez-Cruet et al. | |
| 2008/0208255 A1 | 8/2008 | Siegal | |
| 2008/0221586 A1 | 9/2008 | Garcia-Bengochea | |
| 2008/0221687 A1 | 9/2008 | Viker | |
| 2008/0234732 A1 | 9/2008 | Landry | |
| 2008/0234733 A1 | 9/2008 | Scrantz | |
| 2008/0243126 A1 | 10/2008 | Gutierrez | |
| 2008/0243255 A1 | 10/2008 | Butler | |
| 2008/0249628 A1 | 10/2008 | Altarac | |
| 2008/0255563 A1 | 10/2008 | Farr | |
| 2008/0255574 A1* | 10/2008 | Dye | 606/99 |
| 2008/0269904 A1* | 10/2008 | Voorhies | 623/17.16 |
| 2008/0306488 A1 | 12/2008 | Altarac | |
| 2008/0312743 A1 | 12/2008 | Vila | |
| 2009/0030423 A1* | 1/2009 | Puno | A61F 2/442 606/99 |
| 2009/0054898 A1 | 2/2009 | Gleason | |
| 2009/0054911 A1 | 2/2009 | Mueller | |
| 2009/0062807 A1 | 3/2009 | Song | |
| 2009/0076607 A1 | 3/2009 | Aalsma | |
| 2009/0088789 A1 | 4/2009 | O'Neil | |
| 2009/0105832 A1 | 4/2009 | Allain et al. | |
| 2009/0112217 A1* | 4/2009 | Hester | 606/99 |
| 2009/0143859 A1 | 6/2009 | McClellan, III | |
| 2009/0164015 A1 | 6/2009 | Liu | |
| 2009/0182431 A1 | 7/2009 | Butler | |
| 2009/0192616 A1 | 7/2009 | Zielinski | |
| 2009/0216234 A1 | 8/2009 | Farr | |
| 2009/0234364 A1 | 9/2009 | Crook | |
| 2009/0240335 A1 | 9/2009 | Arcenio | |
| 2009/0276049 A1* | 11/2009 | Weiland | 623/17.16 |
| 2009/0299479 A1 | 12/2009 | Jones | |
| 2009/0317278 A1 | 12/2009 | Kokubo | |
| 2010/0016968 A1 | 1/2010 | Moore | |
| 2010/0030217 A1 | 2/2010 | Mitusina | |
| 2010/0076502 A1 | 3/2010 | Guyer | |
| 2010/0094422 A1* | 4/2010 | Hansell et al. | 623/17.16 |
| 2010/0100098 A1 | 4/2010 | Norton | |
| 2010/0125334 A1 | 5/2010 | Krueger | |
| 2010/0161060 A1 | 6/2010 | Schaller | |
| 2010/0174321 A1 | 7/2010 | Schaller | |
| 2010/0185290 A1 | 7/2010 | Compton | |
| 2010/0191241 A1 | 7/2010 | McCormack | |
| 2010/0191337 A1 | 7/2010 | Zamani | |
| 2010/0198263 A1 | 8/2010 | Siegal | |
| 2010/0211076 A1 | 8/2010 | Germain | |
| 2010/0211107 A1 | 8/2010 | Muhanna | |
| 2010/0217269 A1* | 8/2010 | Landes | 606/84 |
| 2010/0217394 A1 | 8/2010 | Michelson | |
| 2010/0234849 A1 | 9/2010 | Bouadi | |
| 2010/0249935 A1 | 9/2010 | Slivka | |
| 2010/0256768 A1 | 10/2010 | Lim | |
| 2010/0274358 A1 | 10/2010 | Mueller et al. | |
| 2010/0280619 A1 | 11/2010 | Yuan | |
| 2010/0305700 A1* | 12/2010 | Ben-Arye et al. | 623/17.11 |
| 2010/0305704 A1 | 12/2010 | Messerli | |
| 2010/0331845 A1 | 12/2010 | Foley | |
| 2011/0004216 A1 | 1/2011 | Amendola | |
| 2011/0009970 A1* | 1/2011 | Puno | 623/17.16 |
| 2011/0029083 A1 | 2/2011 | Hynes | |
| 2011/0029085 A1 | 2/2011 | Hynes | |
| 2011/0035011 A1 | 2/2011 | Cain | |
| 2011/0054529 A1 | 3/2011 | Michelson | |
| 2011/0054621 A1 | 3/2011 | Lim | |
| 2011/0093078 A1 | 4/2011 | Puno | |
| 2011/0106259 A1 | 5/2011 | Lindenmann et al. | |
| 2011/0106260 A1 | 5/2011 | Laurence | |
| 2011/0112586 A1 | 5/2011 | Guyer | |
| 2011/0125266 A1 | 5/2011 | Rodgers | |
| 2011/0190891 A1 | 8/2011 | Suh et al. | |
| 2011/0196501 A1 | 8/2011 | Michelson | |
| 2011/0276142 A1* | 11/2011 | Niemiec et al. | 623/17.16 |
| 2011/0282459 A1 | 11/2011 | McClellan, III | |
| 2011/0301712 A1 | 12/2011 | Palmatier et al. | |
| 2011/0319898 A1 | 12/2011 | O'Neil | |
| 2011/0319899 A1 | 12/2011 | O'Neil | |
| 2011/0319998 A1* | 12/2011 | O'Neil et al. | 623/17.16 |
| 2011/0319999 A1 | 12/2011 | O'Neil | |
| 2011/0320000 A1 | 12/2011 | O'Neil | |
| 2012/0035730 A1* | 2/2012 | Spann | 623/17.16 |
| 2012/0130387 A1* | 5/2012 | Simpson et al. | 606/104 |
| 2012/0165943 A1* | 6/2012 | Mangione et al. | 623/17.16 |
| 2012/0209383 A1* | 8/2012 | Tsuang et al. | 623/17.12 |
| 2012/0277877 A1 | 11/2012 | Smith | |
| 2012/0310352 A1 | 12/2012 | DiMauro et al. | |
| 2013/0006362 A1* | 1/2013 | Biedermann et al. | 623/17.16 |
| 2013/0023937 A1* | 1/2013 | Biedermann et al. | 606/279 |
| 2013/0035762 A1 | 2/2013 | Siegal | |
| 2013/0079790 A1* | 3/2013 | Stein | A61F 2/4611 606/102 |
| 2013/0109925 A1 | 5/2013 | Horton | |
| 2013/0110239 A1 | 5/2013 | Siegal et al. | |
| 2013/0116791 A1 | 5/2013 | Theofilos | |
| 2013/0138214 A1 | 5/2013 | Greenhalgh | |
| 2013/0150906 A1* | 6/2013 | Kerboul | A61F 2/4611 606/86 A |
| 2013/0173004 A1 | 7/2013 | Greenhalgh | |
| 2013/0190875 A1 | 7/2013 | Shulock | |
| 2013/0238006 A1 | 9/2013 | O'Neil | |
| 2013/0253652 A1 | 9/2013 | Michelson | |
| 2013/0268077 A1* | 10/2013 | You et al. | 623/17.16 |
| 2013/0310937 A1 | 11/2013 | Pimenta | |
| 2014/0025170 A1 | 1/2014 | Lim | |
| 2014/0039626 A1* | 2/2014 | Mitchell | 623/17.16 |
| 2014/0039627 A1 | 2/2014 | Weiland | |
| 2014/0052259 A1 | 2/2014 | Garner et al. | |
| 2014/0058512 A1* | 2/2014 | Petersheim | 623/17.16 |
| 2014/0058513 A1* | 2/2014 | Gahman et al. | 623/17.16 |
| 2014/0142704 A1 | 5/2014 | Ralph | |
| 2014/0153065 A1 | 6/2014 | Mori | |
| 2014/0172103 A1* | 6/2014 | O'Neil et al. | 623/17.16 |
| 2014/0172105 A1* | 6/2014 | Frasier et al. | 623/17.16 |
| 2014/0193798 A1 | 7/2014 | Mills | |
| 2015/0032212 A1 | 1/2015 | O'Neil | |
| 2015/0094812 A1 | 4/2015 | Cain | |
| 2015/0150691 A1 | 6/2015 | Lim | |
| 2015/0196400 A1 | 7/2015 | Dace | |
| 2015/0257898 A1 | 9/2015 | Weiland | |
| 2016/0038306 A1 | 2/2016 | O'Neil | |
| 2017/0128231 A1 | 5/2017 | O'Neil | |

FOREIGN PATENT DOCUMENTS

| | | |
|---|---|---|
| DE | 10241948 | 4/2004 |
| DE | 10357960 | 7/2005 |
| EP | 346129 | 12/1989 |
| EP | 356112 | 2/1990 |
| EP | 0425542 | 8/1991 |
| EP | 637439 | 2/1995 |
| EP | 0641547 | 8/1995 |
| EP | 734702 | 10/1996 |
| EP | 557686 | 9/1997 |
| EP | 609084 | 9/1997 |
| EP | 419564 | 8/1998 |
| EP | 855886 | 8/1998 |
| EP | 720455 | 1/2002 |
| EP | 712607 | 2/2002 |
| EP | 615428 | 3/2002 |
| EP | 752830 | 6/2002 |
| EP | 1222898 | 7/2002 |
| EP | 1222898 | 8/2002 |
| EP | 1265562 | 12/2002 |
| EP | 916323 | 1/2003 |
| EP | 1294321 | 3/2003 |
| EP | 812167 | 5/2003 |
| EP | 703757 | 8/2003 |

(56) References Cited

FOREIGN PATENT DOCUMENTS

| | | |
|---|---|---|
| EP | 855887 | 8/2003 |
| EP | 1221914 | 9/2003 |
| EP | 1283026 | 9/2003 |
| EP | 1219248 | 1/2004 |
| EP | 1219268 | 1/2004 |
| EP | 1344509 | 2/2004 |
| EP | 1391188 | 2/2004 |
| EP | 831759 | 3/2004 |
| EP | 1092395 | 4/2004 |
| EP | 1405602 | 4/2004 |
| EP | 1129668 | 5/2004 |
| EP | 1374806 | 6/2004 |
| EP | 901351 | 8/2004 |
| EP | 836457 | 9/2004 |
| EP | 814718 | 11/2004 |
| EP | 1093760 | 11/2004 |
| EP | 1197181 | 11/2004 |
| EP | 732093 | 12/2004 |
| EP | 1124510 | 12/2004 |
| EP | 1488755 | 12/2004 |
| EP | 1508307 | 2/2005 |
| EP | 988003 | 5/2005 |
| EP | 1346695 | 12/2005 |
| EP | 1605836 | 12/2005 |
| EP | 1221915 | 2/2006 |
| EP | 1389983 | 8/2006 |
| EP | 1684675 | 8/2006 |
| EP | 1009338 | 10/2006 |
| EP | 1709920 | 10/2006 |
| EP | 1722722 | 11/2006 |
| EP | 1308132 | 12/2006 |
| EP | 1374806 | 12/2006 |
| EP | 1525863 | 1/2007 |
| EP | 1764066 | 3/2007 |
| EP | 840580 | 4/2007 |
| EP | 1009337 | 6/2007 |
| EP | 1514519 | 7/2007 |
| EP | 1618848 | 7/2007 |
| EP | 1442732 | 9/2007 |
| EP | 1829486 | 9/2007 |
| EP | 1153574 | 2/2008 |
| EP | 1290985 | 4/2008 |
| EP | 1302182 | 8/2008 |
| EP | 1437105 | 10/2008 |
| EP | 1905931 | 12/2008 |
| EP | 1829503 | 9/2009 |
| EP | 1383449 | 11/2009 |
| EP | 1439773 | 1/2010 |
| EP | 1905391 | 1/2010 |
| EP | 1437988 | 3/2010 |
| EP | 1500372 | 3/2010 |
| EP | 1596764 | 3/2010 |
| EP | 1841385 | 3/2010 |
| EP | 1549259 | 4/2010 |
| EP | 1762202 | 1/2011 |
| EP | 1400221 | 9/2011 |
| EP | 1833428 | 4/2012 |
| EP | 1653892 | 4/2013 |
| EP | 1905390 | 7/2013 |
| EP | 2058014 | 8/2015 |
| EP | 2016924 | 3/2017 |
| FR | 2703580 | 10/1994 |
| FR | 2736537 | 1/1997 |
| FR | 2738475 | 3/1997 |
| FR | 2703580 | 10/1997 |
| FR | 2817463 | 4/2003 |
| FR | 2841125 | 12/2003 |
| FR | 2874814 | 3/2006 |
| FR | 2948277 | 1/2011 |
| JP | 2006-508714 | 3/2006 |
| JP | 2006-516456 | 7/2006 |
| JP | 2007-501027 | 1/2007 |
| JP | 2007-517539 | 7/2007 |
| JP | 2010-538683 | 12/2010 |
| WO | WO 89/09035 | 10/1989 |
| WO | WO 1992014423 | 9/1992 |
| WO | WO 93/01771 | 2/1993 |
| WO | WO 95/26164 | 5/1994 |
| WO | WO 95/20370 | 3/1995 |
| WO | WO 95/08964 | 4/1995 |
| WO | WO 95/15133 | 6/1995 |
| WO | WO 96/40015 | 12/1996 |
| WO | WO 1997/014377 | 4/1997 |
| WO | WO 97/37620 | 10/1997 |
| WO | WO 97/20526 | 12/1997 |
| WO | WO 98/17208 | 4/1998 |
| WO | WO 1998034568 | 8/1998 |
| WO | WO 99/09896 | 4/1999 |
| WO | WO 1999060956 | 12/1999 |
| WO | WO 1999063914 | 12/1999 |
| WO | WO 2000024343 | 5/2000 |
| WO | WO 2000074605 | 12/2000 |
| WO | WO 2001/068005 | 9/2001 |
| WO | WO 2001/095838 | 12/2001 |
| WO | WO 2002003870 | 1/2002 |
| WO | WO 2002/017823 | 3/2002 |
| WO | WO 2003003951 | 1/2003 |
| WO | WO 2004000176 | 12/2003 |
| WO | WO 2004000177 | 2/2004 |
| WO | WO 2004080316 | 9/2004 |
| WO | WO 2004069033 | 1/2005 |
| WO | WO 2005/011539 | 2/2005 |
| WO | WO 2005/041825 | 5/2005 |
| WO | WO 2005/087143 | 9/2005 |
| WO | WO 2005094297 | 10/2005 |
| WO | WO 20060449202 | 4/2006 |
| WO | WO 2006/079356 | 8/2006 |
| WO | WO 2006118944 | 11/2006 |
| WO | WO 2007/016801 | 2/2007 |
| WO | WO 2007048012 | 4/2007 |
| WO | WO 2007/070751 | 6/2007 |
| WO | WO 2007/093900 | 8/2007 |
| WO | WO 2008005627 | 1/2008 |
| WO | WO 2008/036636 | 3/2008 |
| WO | WO 2006072941 | 7/2008 |
| WO | WO 2008/079953 | 10/2008 |
| WO | WO 2010011348 | 1/2010 |
| WO | WO 2010075555 | 10/2010 |
| WO | WO 2010121002 | 12/2010 |
| WO | WO 2011013047 | 4/2011 |
| WO | WO 2011/056172 | 5/2011 |
| WO | WO 2011060087 | 5/2011 |
| WO | WO 2012129197 | 9/2012 |
| WO | WO 2013149611 | 10/2013 |
| WO | WO 2012027490 | 3/2014 |
| WO | WO 2012103254 | 4/2014 |

OTHER PUBLICATIONS

Allcock, "Polyphosphazenes"; *The Encyclopedia of Polymer Science*; 1988; pp. 31-41; vol. 13; Wiley Intersciences, John Wiley & Sons.

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Heller, "Poly (Otrho Esters)"; *Handbook of Biodegradable Polymers;*edited by Domb; et al; Hardwood Academic Press; 1997; pp. 99-118.

Kemnitzer, "Degradable Polymers Derived From the Amino Acid L-Tyrosine"; 1997; pp. 251-272; edited by Domb, et. al., Hardwood Academic Press.

Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.

U.S. Appl. No. 61/009,546, filed Dec. 28, 2007 Rodgers.

U.S. Appl. No. 61/140,926, filed Dec. 26, 2008 Spann.

U.S. Appl. No. 61/178,315, filed May 14, 2009 Spann.

Synthes Spine, "OPAL Spaper System. Oblique posterior atraumatic lumbar spacer system, Technique Guide" (Brochure), 2008, US.

(56) References Cited

OTHER PUBLICATIONS

Synthes Spine, "T-PLIF Spacer Instruments, Technique Guide" (Brochure), 2001, US.
Synthes Spine, "Vertebral Spaer—TR" (Brochure), 2002, US.
Synthes Spine,"Vertebral Spacer—PR. Vertebral body replacement device intended for use in the thoracolumbar spine" (Brochure), 2002, US.
AcroMed Carbon Fiber Interbody Fusion Devices; Jan. 1998, 8 pages.
Al-Sanabani, Application of Calcium Phosphate Materials in Dentistry, vol. 2013, Int. J. Biomaterials, 1-12, 2013.
Bailey, Stabilzation of the Cervical Spine by Anterior Fusion, 42-A(4), J. Bone Joint Surg.,565-594, Jun. 1960.
Banward, Iliac Crest Bone Graft Harvest Donor Site Morbidity, 20 (9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan I/F Cage for PLIF Surgical Technique Guide; Apr. 1991, 22 pages.
Brantigan, Interbody Lumbar Fusion Using a Carbon Fiber Cage Implant Versus Allograft Bone, 19(13) Spine 1436-1444, 1994.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Carbon Fiber Composite Ramps for Lumbar Interbody Fusion; Apr. 1997, 2 pages.
Cloward, Gas-Sterilized Cadaver Bone Grafts for Spinal Fusion Operations, 5(1), Spine 4-10, Jan./Feb. 1980.
Cloward, The Anterior Approach for Removal of Ruptured Cervical Disks, vol. 15, J. Neuro.602-617, 1958.
Dabrowski, Highly Porous Titanium Scaffolds for Orthopaedic Applications, J. Biomed Mater. Res. B. Appl. Biomat Oct.;95(1):53-61, 2010.
Delecrin, Morbidite du Prelevement de Greffons osseuz au Niveau des Cretes Iliaques dansla Chirurgie Du Rachis; Justification du recours aux substituts osseuz, 13(3) Rachis 167-174, 2001 (w/Translation).
DePuy Motech Surgical Titanium Mesh Brochure; 1998, 13 pages.
Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly 1997); http://www.thebarrow.org/Education And Resources/Barrow Quarterly/204837.
Enker, Interbody Fusion and Instrumentation, No. 300 Clin. Orth. Rei. Res. 90-101, Mar. 1994.
Fassio, Use of Cervical Plate-Cage PCB and Results for Anterior Fusion in Cervical Disk Syndrome, 15(6) Rachis 355-361 Dec. 2003 Translation.
Fowler, Complications Associated with Harvesting Autogenous Iliac Bone Graft, 24(12) Am. J. Ortho. 895-904, Dec. 1995.
Fuentes, Les Complications de Ia Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/ translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.

Huttner, Spinal Stenosis & Posterior Lumbar Interbody Fusion, No. 193, Clinical Ortho Rei. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NOT in Aerospace,2012, 9 pages.
Khan, Chapter 2—Implantable Medical Devices, Focal Controlled Drug Delivery, Advancesin Delivery Science and Technology, A.J. Domb and W. Khan (eds.) 2014.
Kozak, Anterior Lumbar Fusion Options, No. 300, Clin. Orth. Rei. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci.,4033-4065, 2009.
Malca, CervicalInterbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117 2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Takahama, A New Improved Biodegradable Tracheal Prosthesis Using Hydroxy Apatite and Carbon Fiber 35(3) ASAIO Trans, 291-293, Jui.-Sep. 1989.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervicai,16(S2) Neurochirurgie 1-212; 1970 (w/Translation).
Wang, Determination of Cortical Bone Porosity and Pore Size Distribution using a Low Field Pulsed NMR Approach, J. Orthop Res., Mar; 21(2):312-9 Mar. 2003.
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.
Synthes History and Evolution of LBIF Brochure; Nov. 2015, 30 pages.
Synthes Spine Cervical Stand-Alone Devices Presentation Brochure; 2010, 40 pages.

\* cited by examiner

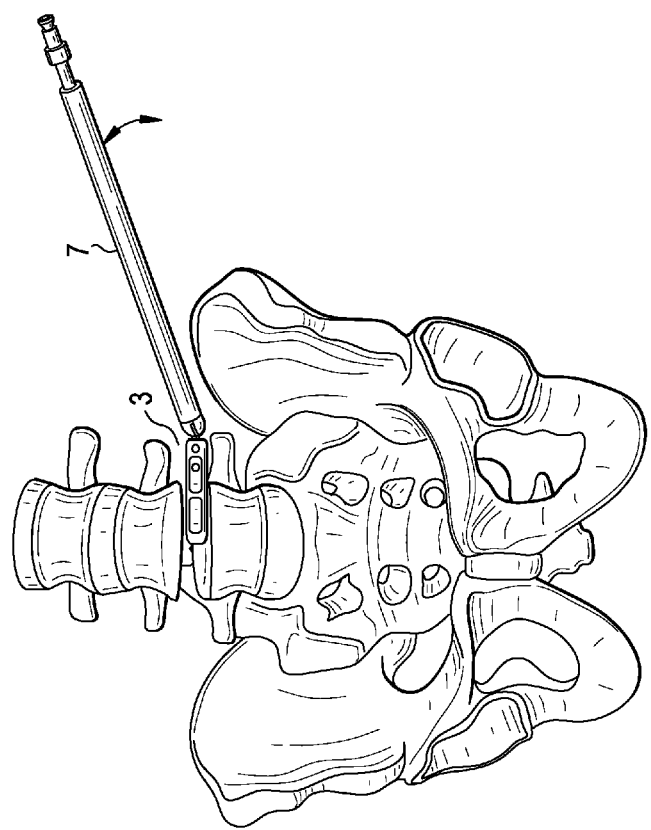
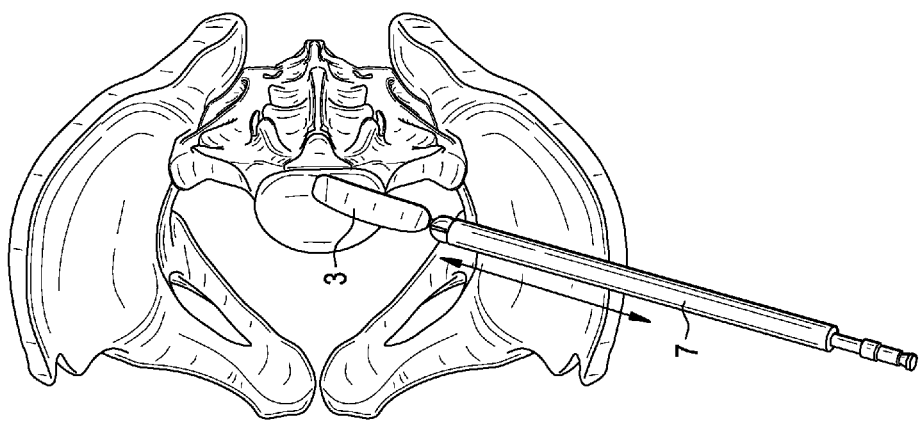
FIG. 2A
FIG. 2B

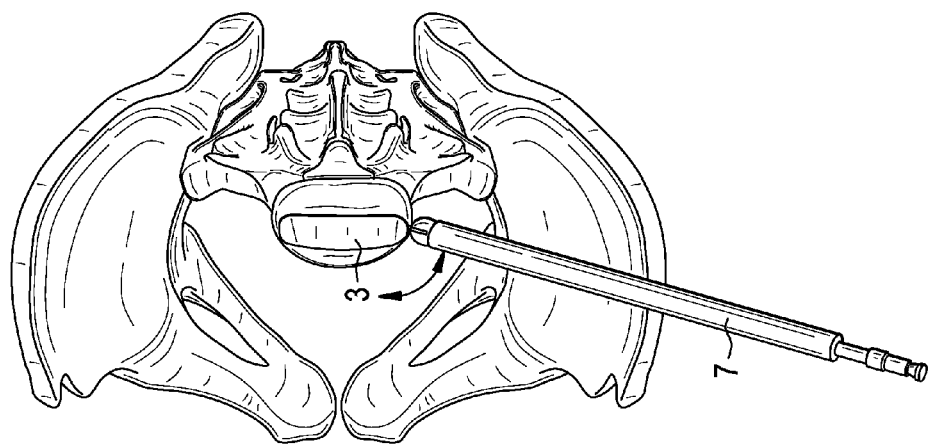
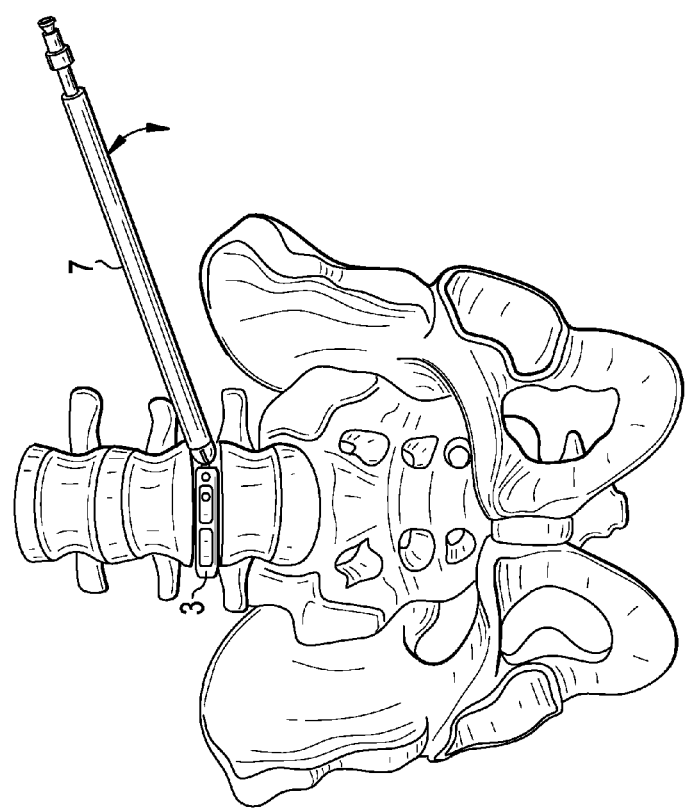

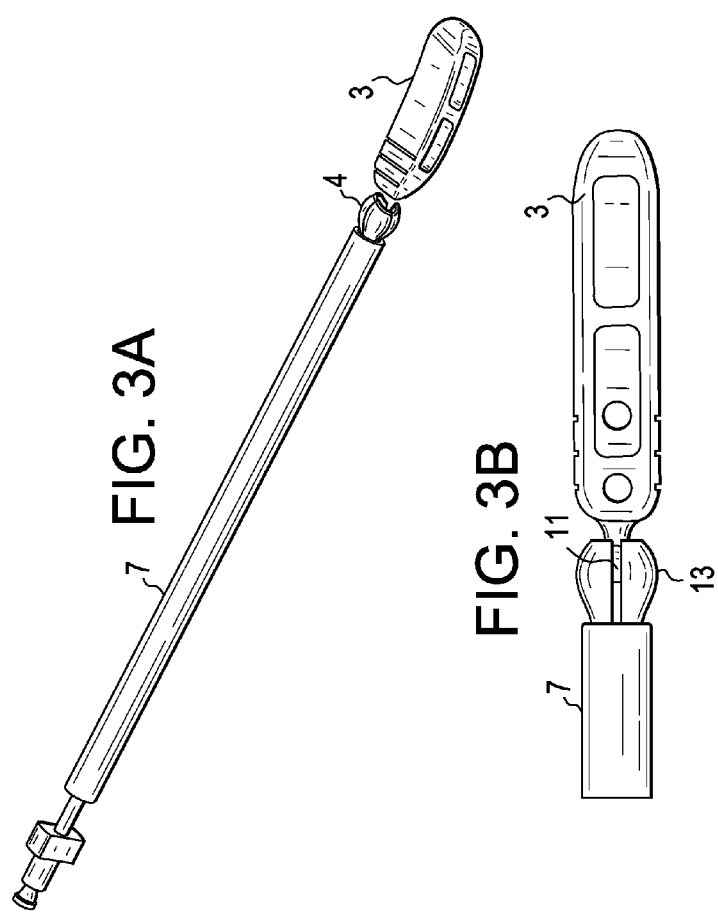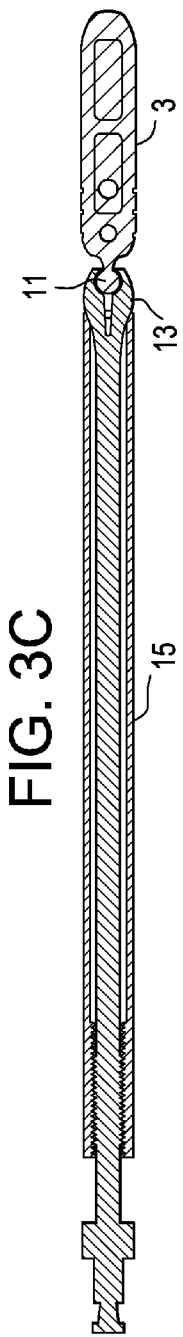

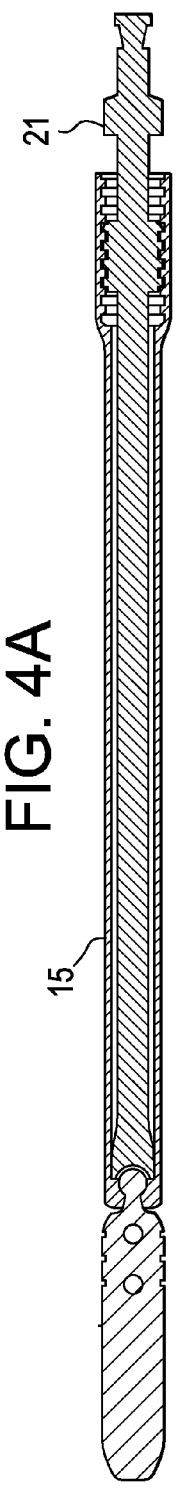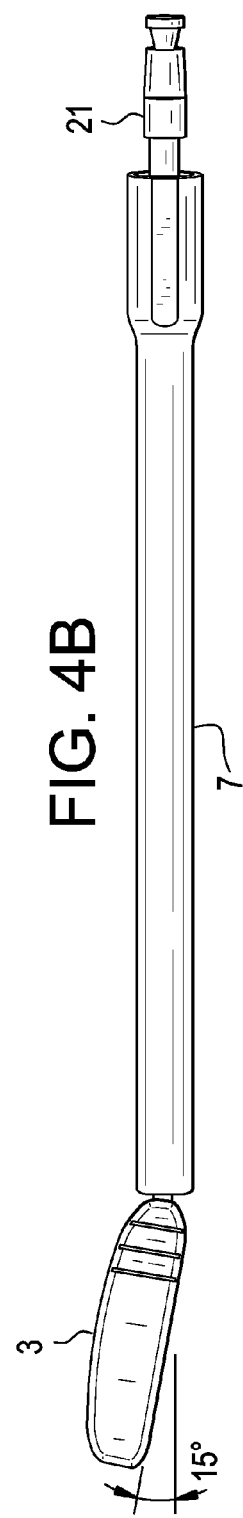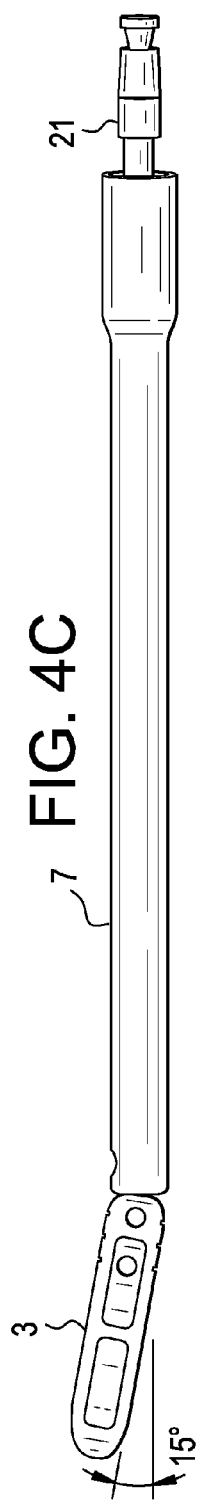

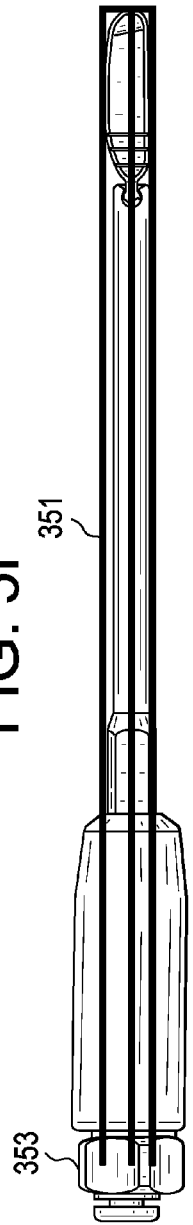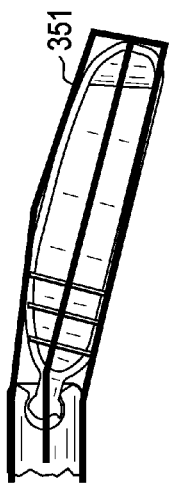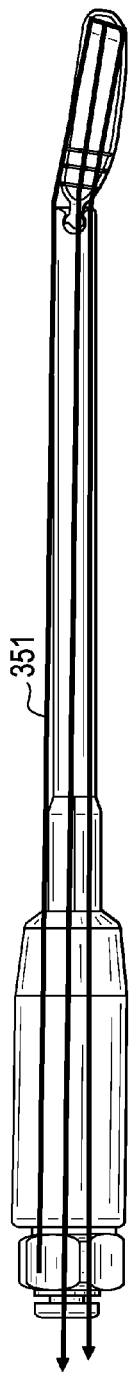
FIG. 5F
FIG. 5G
FIG. 5H
FIG. 5I

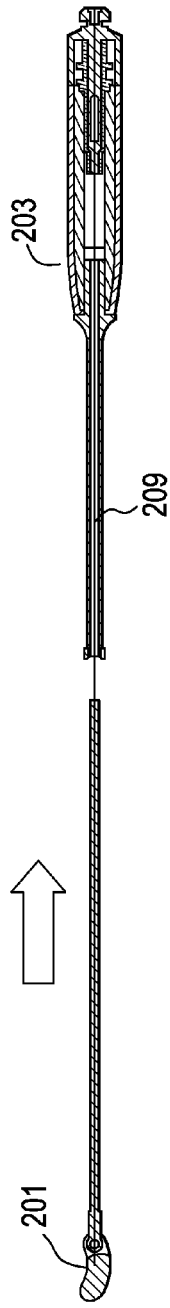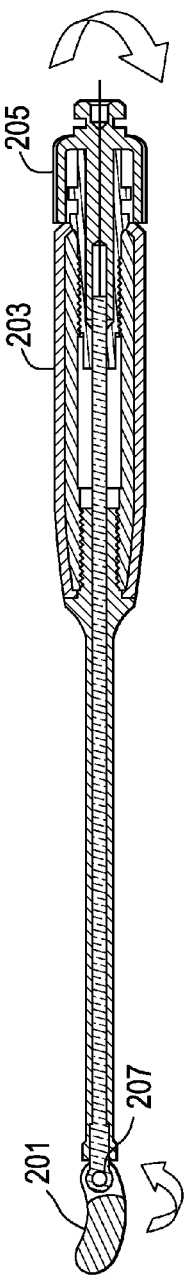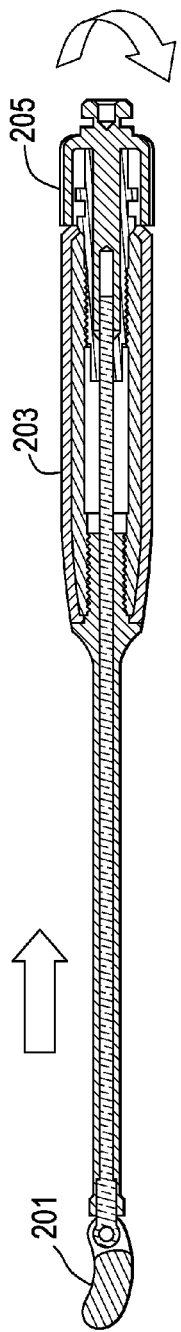

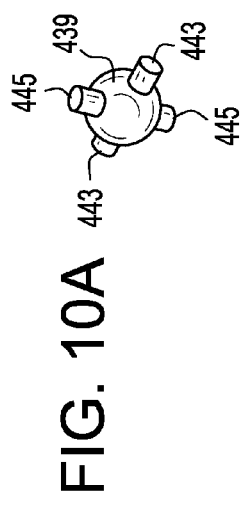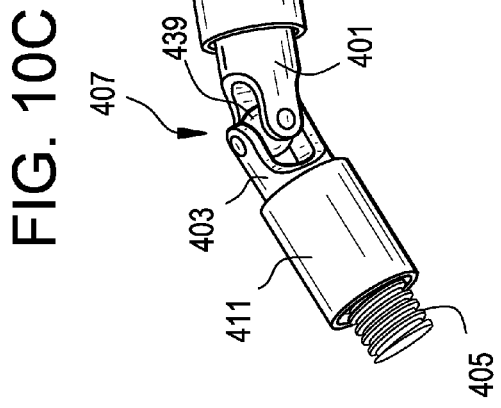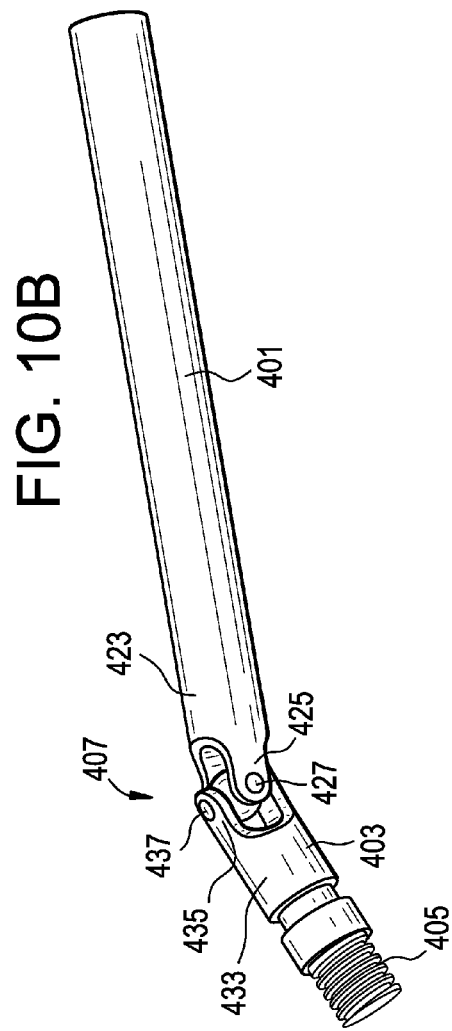

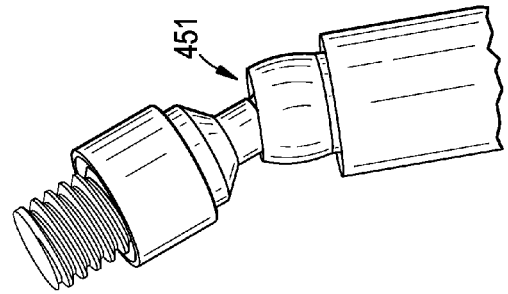
FIG.10G
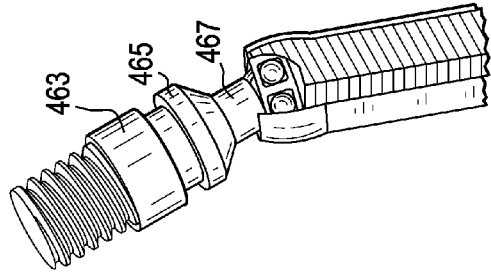
FIG.10F
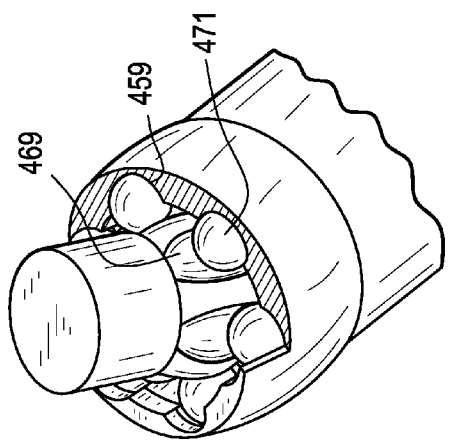
FIG.10H
FIG.10E
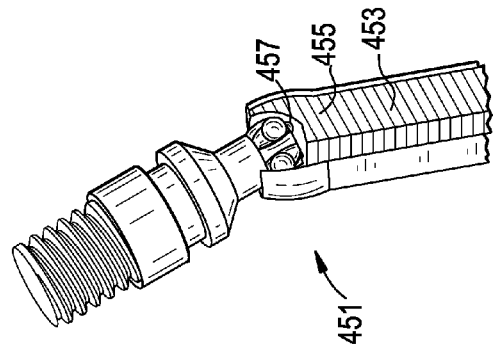
FIG.10D

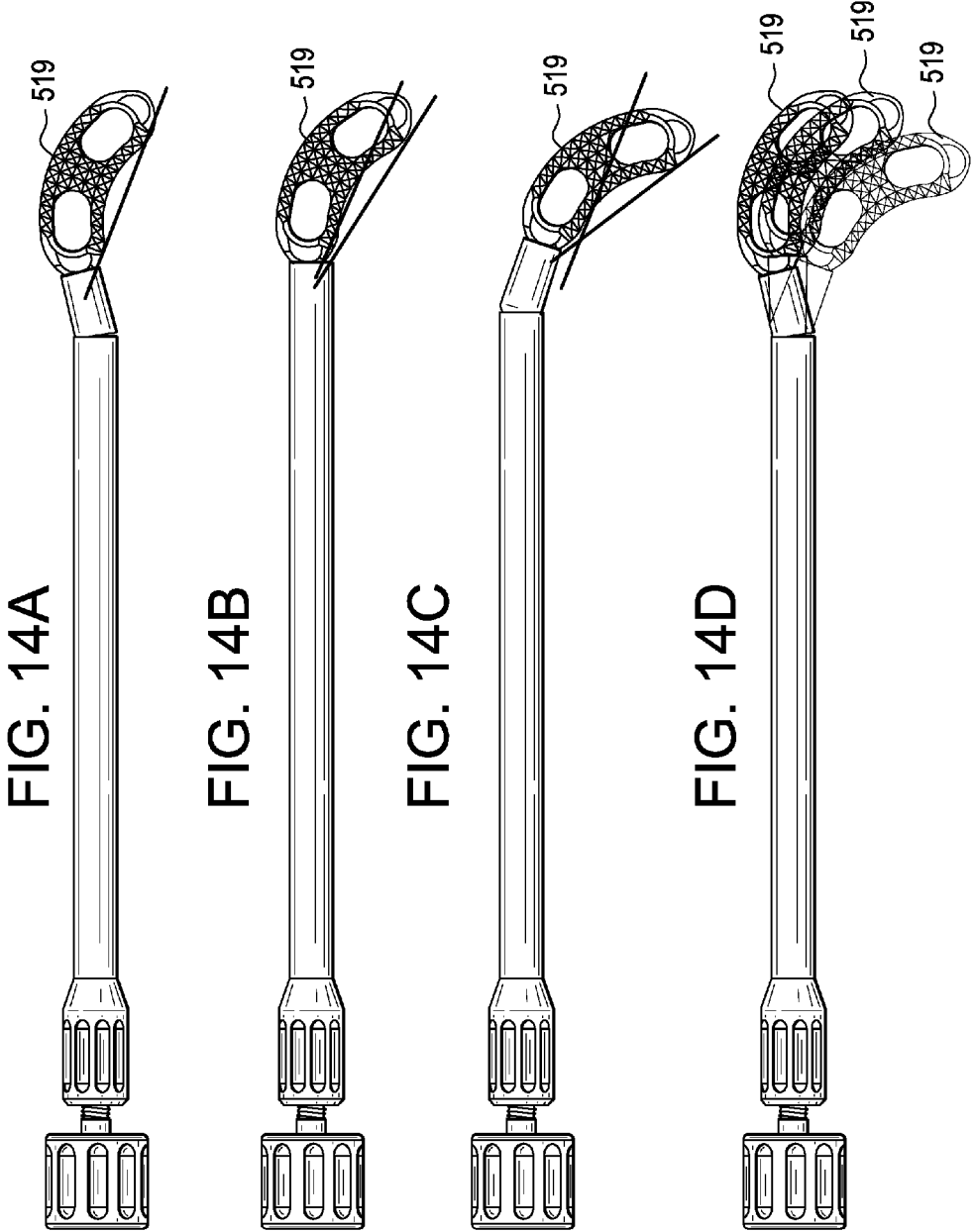

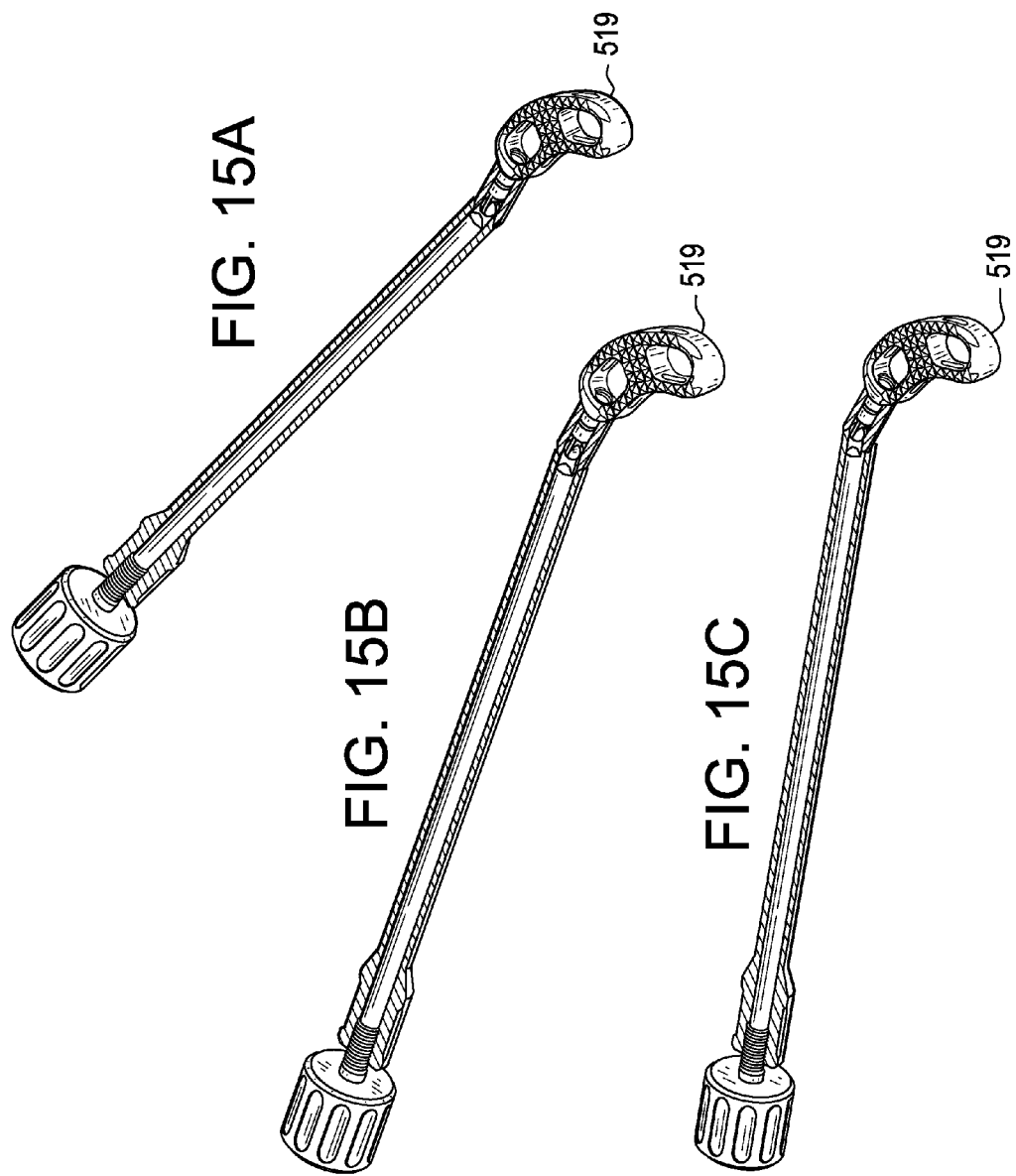

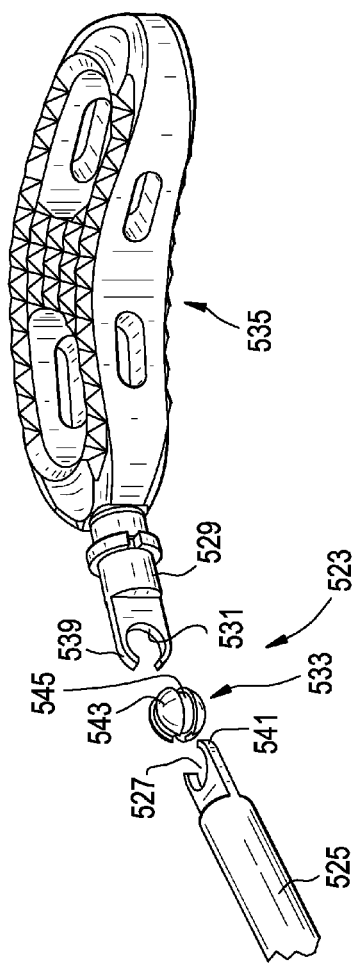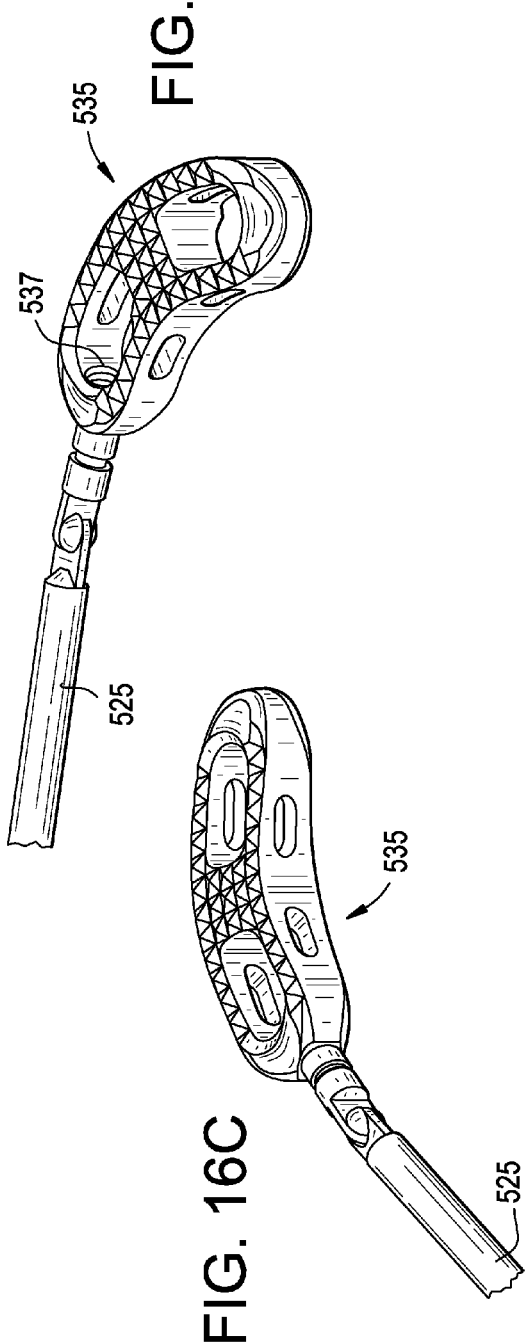

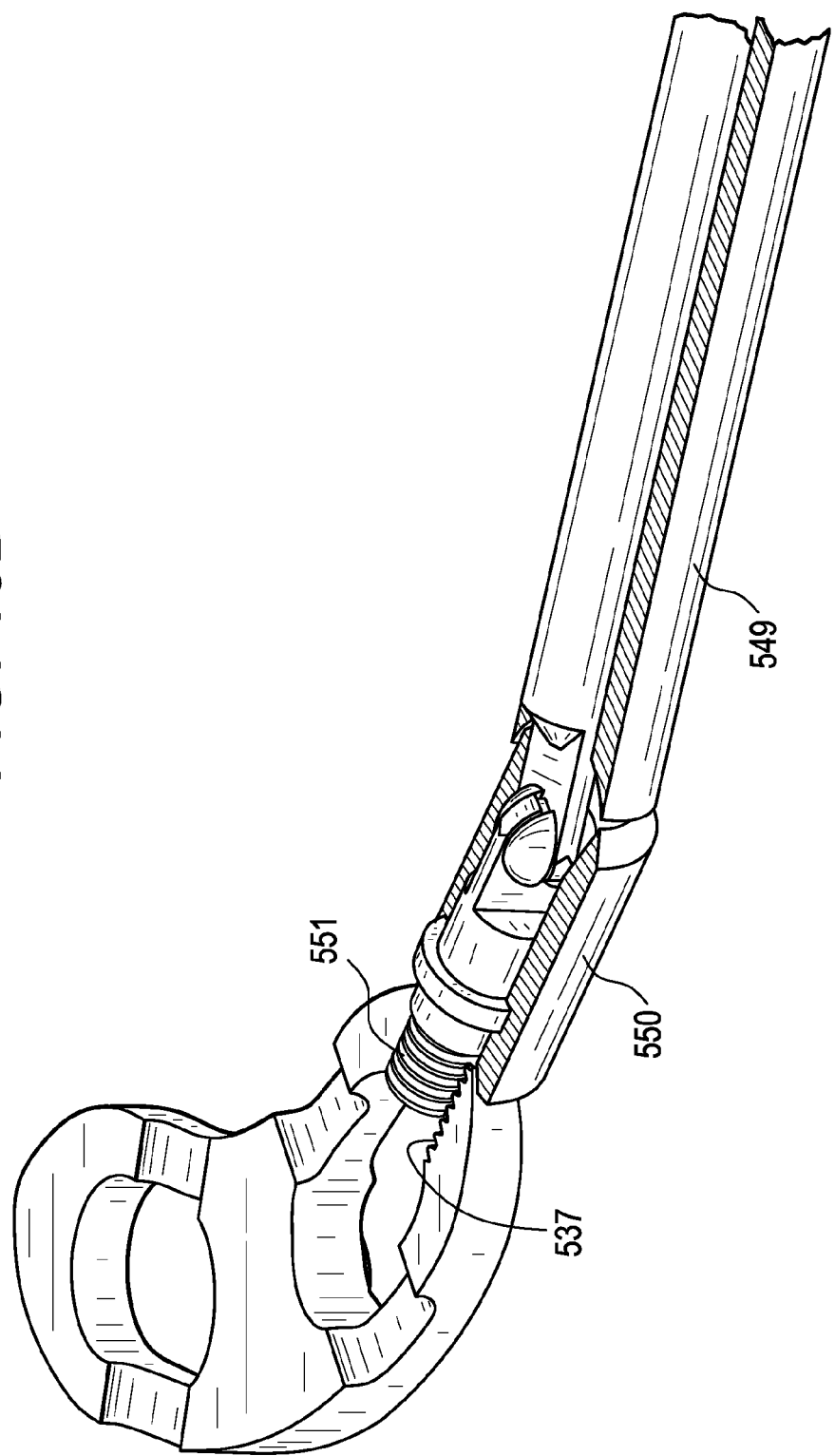

POLYAXIAL ARTICULATING INSTRUMENT

CONTINUITY DATA

This application claims priority from provisional patent application U.S. Ser. No. 61/738,078, filed Dec. 17, 2012, entitled "Polyaxial Articulating Tool", Frasier et al., the specification of which is hereby incorporated by reference in its entirety.

BACKGROUND OF THE INVENTION

Before an intervertebral implant is inserted into the intervertebral disc space of a patient, there is often the need to assess the adequacy of the disc space and the implant by first inserting a trial device into the disc space.

Currently, no conventional trial system allows for determination of the angle of the implanted trial following its satisfactory placement and imaging.

US Patent Publication No. 2012-0035730 (Spann) discloses a method for introducing a spinal disc implant into an intervertebral space of a subject. The subject is placed in a lateral position, and the anterior face of the spinal disc intervertebral space is accessed, between the L5 and S1 vertebrae, from an anterior and lateral retroperitoneal approach. An operative corridor to the anterior face of the spinal disc space is established by introducing a retractor instrument anterolaterally to the spinal disc space between the anterior superior iliac spine and the anterior inferior iliac spine. The damaged spinal disc contents are removed from the intervertebral space through the operative corridor, and the implant is advanced into the intervertebral space at an oblique angle and pivoted to position the implant substantially laterally within the intervertebral space. Elongated retractor and insertion instruments, as well as a modified disc implant, are also disclosed for carrying out the method. See Spann at FIGS. 13-14.

US Patent Publication No. 2011-0009970 (Puno) discloses a system for implanting an inter-body device between adjacent vertebrae comprises an inter-body device having a plurality of cans secured to a flexible bridge and having a relief portion therebetween. An inserter tube and complementary bullnoses are advantageously secured to the vertebrae by an extension arm for securing the assembly precisely in place. A plurality of articulating trial implants are provided to test fit a disc space for the proper sized inter-body device.

US Patent Publication No. 2011-0319998 (DePuy Spine) discloses a polyaxial trial suitable for use in lateral approaches. In particular, it discloses a method comprising the steps of: a) laterally inserting a variable-angle trial into an intervertebral disc space, b) determining an angle set by the trial in the disc space, c) providing the angle to an implant-inserter apparatus, d) inserting the implant into the disc space at the angle.

US Patent Publication No. 2006-0229627 (Hunt) discloses an instrument for use in a procedure for inserting a spinal implant between human vertebrae may include a shaft and an end member. The end member may rotate with respect to the shaft. An angle of the end member with respect to the shaft may be varied when the end member is in a disc space between the human vertebrae. The instrument may include a slide for securing the end member at selected angles relative to the shaft. The end member may be separable from the shaft when the end member is in a selected orientation with the shaft. An instrument kit may include a shaft assembly and modular end members for various steps in a surgical procedure, such as disc space preparation, disc space evaluation, and spinal implant insertion. See in particular Hunt at paragraph [0016] and claim 9.

US Patent Publication No. 2008-0077241 (Nguyen) discloses a method of preparing a pair of adjacent vertebral endplates, involving a surgical instrument having a pivoting distal removable insert, a proximal handle portion, a body portion, and a linkage member positioned between the insert and the proximal handle portion, the insert having a first angular position relative to the body. A leading end of the insert may be placed in a first position between two adjacent vertebral endplates and moved to a second position between the adjacent vertebral endplates by impacting the proximal end portion of the surgical instrument. The insert may be pivoted to a second angular position relative to the body portion by rotating the handle about the body portion and may lock the second angular position of the distal insert. The insert may be moved to a third position between the adjacent vertebral endplates by impacting the proximal end portion of the surgical instrument.

US Patent Publication No. 2008-0065082 (Chang) discloses instruments and methods for inserting a rasp into an intervertebral space of a spine and using the rasp to decorticate the adjacent vertebra. More particularly, one embodiment provides an instrument that actively changes the angle of the rasp relative to the instrument. The delivery instrument may use a gear portion to articulate the rasp. A second gear on the rasp may mate with a corresponding gear on the instrument. As the instrument gear rotates relative to the instrument, the instrument gear drives the rasp gear, thereby rotating the rasp to decorticate the vertebra. Trial inserts and methods are also provided to determine an appropriate size of a rasp for decortication.

US Patent Publication No. 2008-0140085 (Gately) discloses a method to insert a spinal implant into a vertebral space, the method including the steps of: grasping the implant with a distal end of an implant insertion tool; holding a proximal end of the implant insertion tool and inserting the implant toward the vertebral space; and manipulating the proximal end to apply a yaw movement to the implant while the implant is attached to the tool and in the vertebral space.

US 2012-0277877 ("Smith") discloses an intervertebral spacer and an insertion tool providing multiple angles of insertion.

Adjustable TLIF implant inserters are limited in angulation to the axial plane for posterior approach surgeries. These devices do not measure the amount of angulation instilled in the trial. Therefore, there remains a need for adjustable trials that allow for flexion of angles of insertion and measurement of the insertion angle for a lateral trial.

In sum, none of the prior art documents discloses a polyaxial trial for anterior, posterior, transforaminal or anterolateral approaches.

SUMMARY OF THE INVENTION

In one aspect of the present invention, there is provided a polyaxial tool (such as a trial) suitable for preparing or trialing the spinal column including intervertebral disc space and/or vertebral body of a patient. In some embodiments, the tool is used through an anterior, lateral, posterior, transforaminal or anterolateral approach.

Therefore, in accordance with the present invention, there is provided a method of preparing an intervertebral disc space or vertebral body in a spinal column in a patient, comprising the steps of:

a) inserting a polyaxial instrument into the intervertebral disc space or the vertebral body via an approach selected from the group consisting of an anterior approach, a posterior approach, a transforaminal approach and an anterolateral approach to the spinal column, wherein the instrument comprises a distal head and a proximal shaft connected by a polyaxial joint.

Now referring to FIG. 1, the articulating inserter and instrument system includes a base instrument 1 pivotally connected to a instrument or trial head 3 (chosen from a set of interchangeable heads) by an articulating joint. Each head has a distal working tip 5 for performing an operation on the patient's spine. The base instrument includes a shaft 7 attached to proximal handle 9.

Still referring to FIG. 1, the instrument or trial head can pivot in a plane generally parallel to the surgical anatomy body. The articulating inserter and instruments system of the present invention allows the surgeon to select and insert various components at various trajectories for spinal access, disc removal, disc space preparation and trial placement. The ability to set the trial to any angle and then lock the trial at that angle allows the instrument manufacturer to build a smaller number of handles to support a large number of different instruments in a given set. It also allows the surgeon to tailor the angulation of any of the instruments to the exact position desired to access and prepare the surgical site.

In some embodiments, the adjustability of the articulating instrument or trial head allows the surgeon to vary the angle of the trial during its insertion into the disc space. First, the surgeon partially inserts the polyaxial instrument or trial into the spinal column at a first locked angle. Examples of partial insertion are shown in FIGS. 2a-b. Then, once the instrument or trial is partially inserted, the user can loosen the knob (located on the proximal end of the shaft), adjust the shaft of the instrument or trial to a different angle, and lock down that angle. The user then proceeds to continue impacting the instrument or trial set at a different angle. The adjustability of the head may be achieved by the head being pinned to the inner shaft and rotatable around that shaft. Although in some embodiments, the user may choose to lock the shaft at a new angle without allowing any additional rotation, the user may alternatively elect to impact on the end of the shaft while leaving the joint loose, thereby allowing the distal head of the trial to freely turn as it completely enters the disc space. The advantage provided by this freely pivoting instrument or trial head over a straight head is that the freely pivoting head not only forms the path that the implant will follow, it also arrives at the final implant position, thereby allowing for more accurate assessment of the implant's final trajectory and fit in the disc space. Examples of complete trial insertion are shown in FIGS. 2c-d.

Therefore, in accordance with the present invention, there is provided a method of preparing an intervertebral disc space or a vertebral body in a spinal column in a patient, comprising the steps of:
  a) partially inserting an articulating instrument into the intervertebral disc space or vertebral body, wherein the articulating instrument comprises a distal head and a proximal shaft connected by an articulating joint held locked at an angle,
  b) loosening the joint,
  c) adjusting the shaft of the instrument to a different angle,
  d) locking the shaft at the different angle, and then
  e) impacting on the shaft without allowing any additional rotation.

Also in accordance with the present invention, there is provided a method of preparing an intervertebral disc space in a patient, comprising the steps of:
  a) partially inserting a polyaxial instrument into the intervertebral disc space,
   wherein the articulating instrument comprises a distal head and a proximal shaft connected by an articulating joint held locked at a first angle, the proximal shaft having a proximal end connected to a handle,
  b) loosening the joint,
  c) adjusting the shaft of the instrument to a second angle,
  c) leaving the joint loose while impacting the shaft, thereby allowing the distal head to freely turn as it enters the disc space.

Once the instrument or trial head is impacted completely into the disc space, the surgeon is ready to assess its positioning by fluoroscopy. In this case, the handle that attached to the proximal end of the shaft can be removed, thereby leaving behind only a thin shaft on the proximal portion of the trial. This thin shaft produces less flouroscopy scatter than the handle/shaft combination. Alternatively, the shaft can be rotated out of the way of the approach corridor. This rotation (or handle removal) allows additional discectomy to be performed posterior to the trial head while the trial head acts as a spacer.

Once fluoroscopy has been performed, the instrument or trial head may be removed from the spinal column. To remove the instrument or trial head, the handle may be reconnected and pulled proximally. In some embodiments, the joint of the head is kept loose, thereby allowing the head to follow the path it created during insertion. The advantage provided by this freely pivoting head over a straight head is that the freely pivoting head not only forms the path that the implant will follow, it also arrives at the final implant position, thereby allowing for more accurate assessment of the implant's final trajectory and fit in the disc space.

Therefore, in accordance with the present invention, there is provided a method of preparing a spinal column in a patient, comprising the steps of:
  a) inserting a polyaxial instrument into the spinal column, wherein the articulating instrument comprises a distal head and a proximal shaft connected by an articulating joint held locked at an angle, the proximal shaft having a proximal end connected to a handle,
  b) removing the handle from the shaft while the head is partially in the spinal column (e.g., partially in the disc space),
  c) reconnecting the handle while the head is partially in the spinal column (e.g., partially in the disc space).

Although a primary aspect of the invention is a trial or instrument head that pivots in the plane generally parallel to the endplates of the vertebral body, other more polyaxial embodiments of the trial are also contemplated. In particular, these include a pivoting feature that is universal in nature, such as a ball-and-socket joint that could allow the articulation to occur in multiple or infinite planes. This could also be achieved with a universal joint or flexible shaft segment. This type of polyaxial articulation could be locked into place through the use of an outer sleeve or an inner pushshaft that tightens down on the joint in any of these embodiments, such as FIG. 4a. The advantage to this configuration could be realized in procedures beyond a TLIF approach in that the head would be able to angle in multiple planes to avoid anatomy that may be in the way of a direct approach to the spinal column and/or a specific disc space.

DESCRIPTION OF THE FIGURES

FIGS. 2A-B disclose partially inserted trial heads of the present invention.

FIGS. 2C-D disclose substantially completely inserted trial heads of the present invention.

FIGS. 3A-3C and 4A-C disclose various views of a ball and socket joint polyaxial trial of the present invention.

FIGS. 5A-I disclose trial heads situated at different angles from the shaft.

FIGS. 9A-C disclose one method of using a trial of the present invention.

FIGS. 10A-C disclose an inserter having a wholly-contained polyaxial joint.

FIGS. 10D-H disclose a polyaxial inserter with a threaded attachment feature.

FIGS. 14A-D disclose a polyaxial inserter-implant assembly having different angles of orientation.

FIGS. 15A-C disclose a polyaxial inserter-implant assembly having different angles of orientation.

FIGS. 16A-E disclose an embodiment of the polyaxial inserter-implant assemblies.

DETAILED DESCRIPTION OF THE INVENTION

Figure 1:
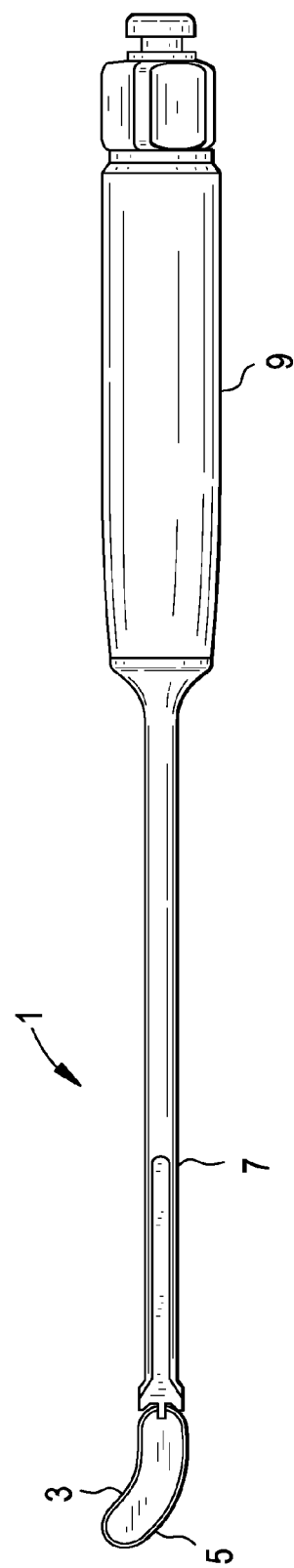
FIG. 1 discloses a single plane inserter of the present invention.
Figure 5A:
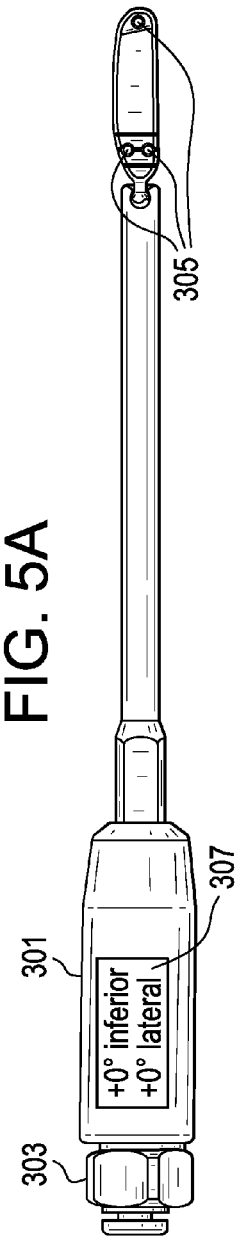
Figure 5B:
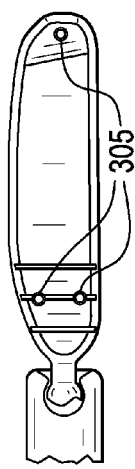
Figure 5C:
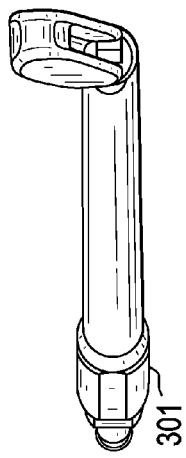
Figure 5D:
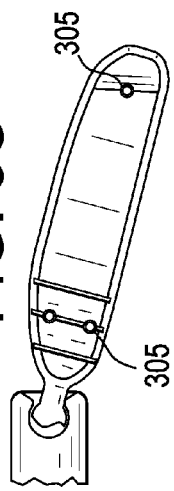
Figure 5E:
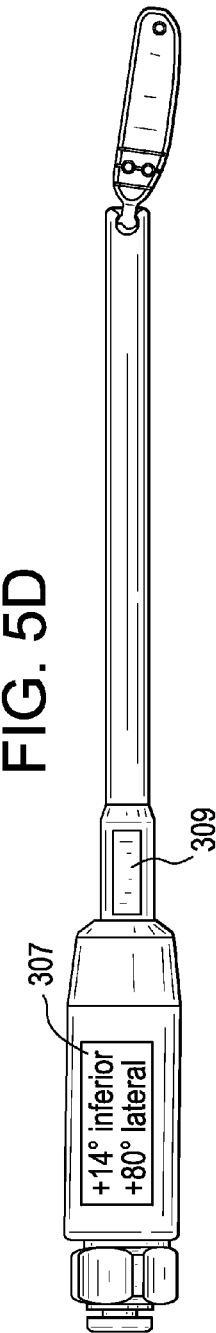
Figure 6B:
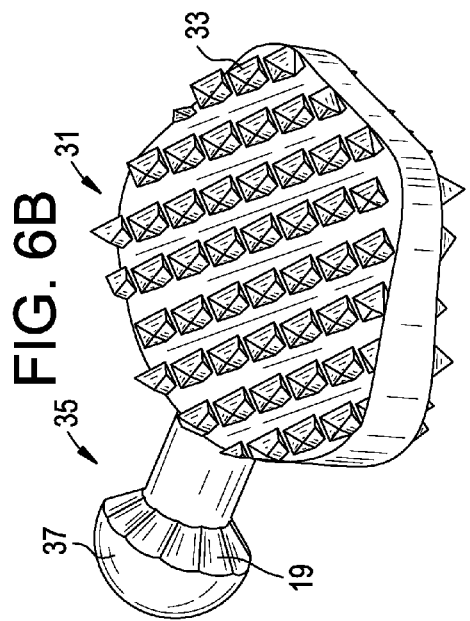
FIGS. 6A-D disclose trial heads of the present invention having facets.
Figure 6D:
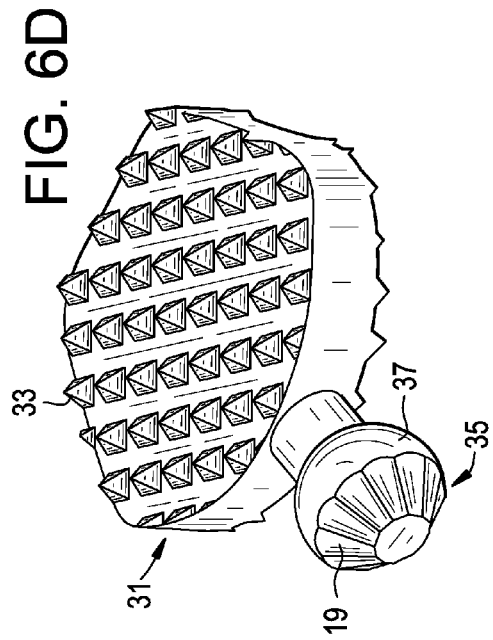
Figure 6A:
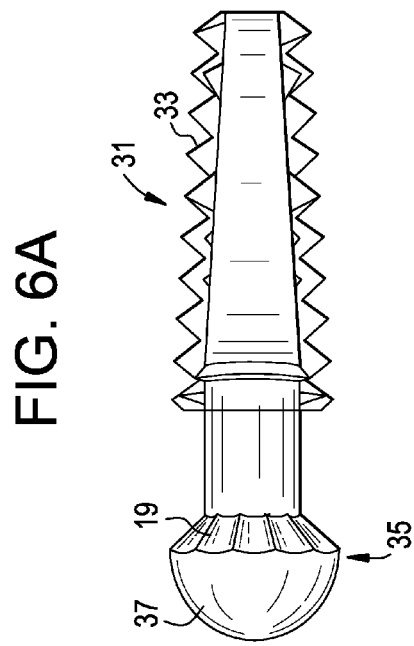
Figure 6C:
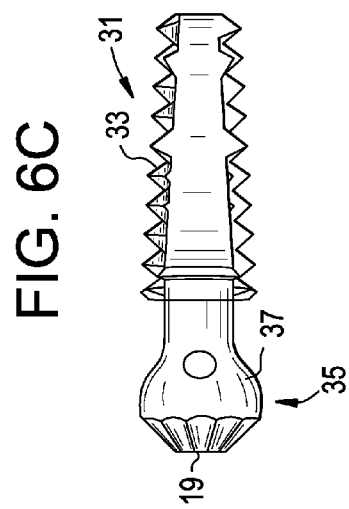
Figure 7A:
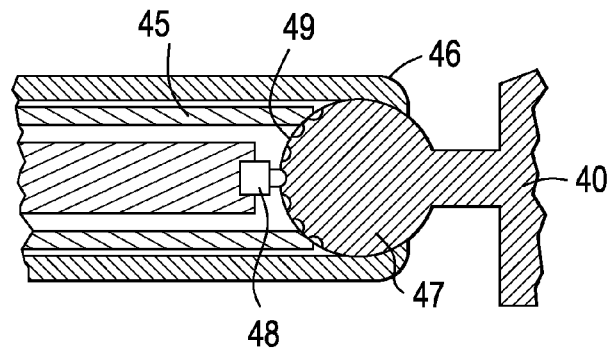
FIGS. 7A-E discloses a steerable polyaxial joint of the present invention.
Figure 7B:
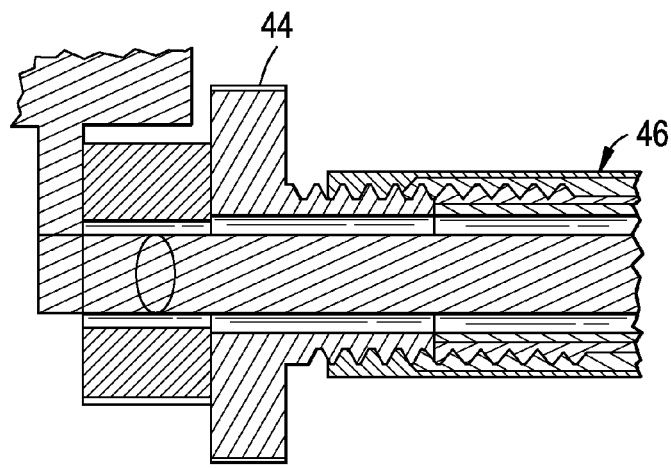
Figure 7E:
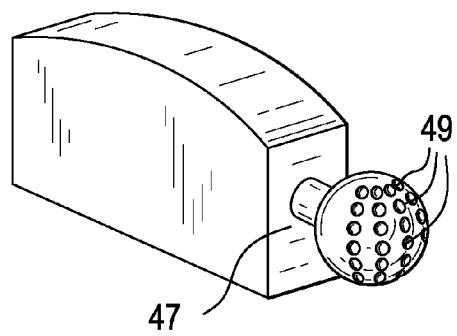
Figure 7C:
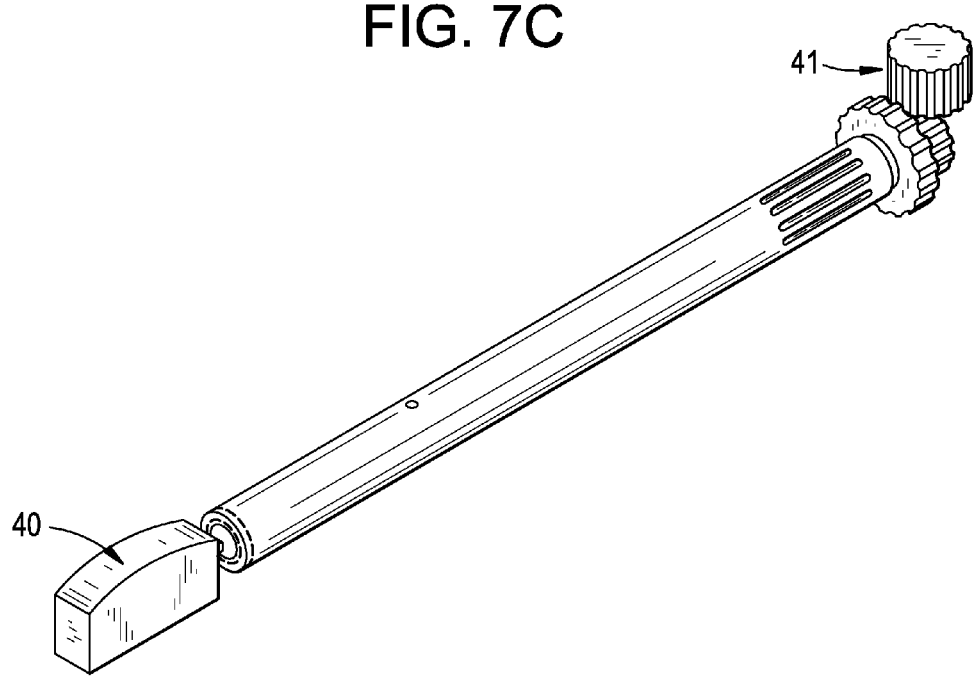
Figure 7D:
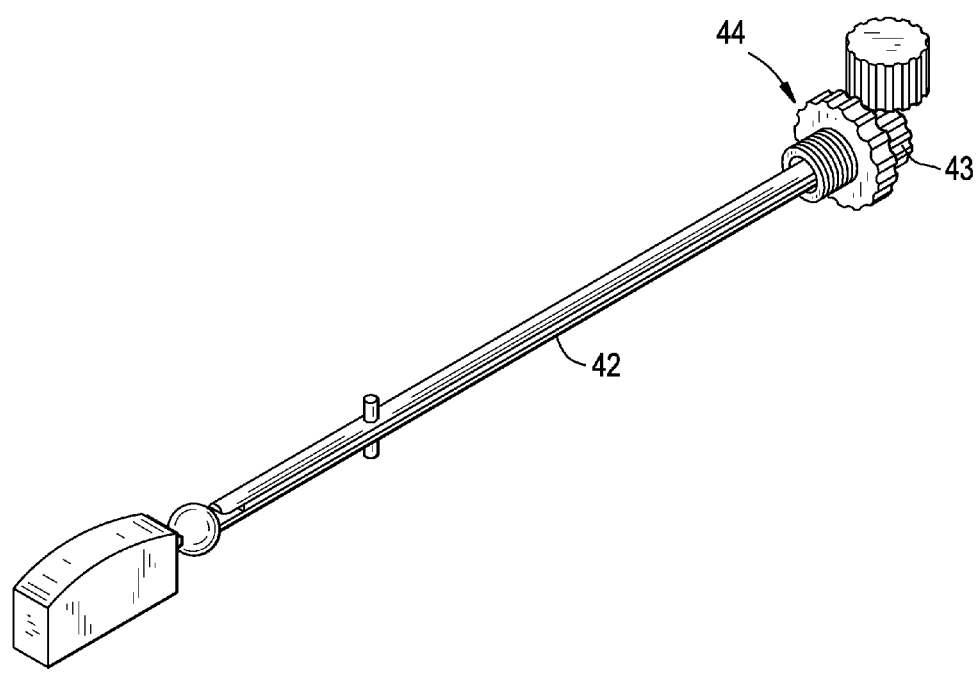

Now referring to FIGS. 3A-5I, the articulating inserter instrument can pivot via articulation features that are universal in nature, allowing the articulation to occur in multiple or infinite planes, such as through a ball-and-socket joint 4. In FIG. 3*b*, the ball 11 forms the proximal portion of trial head, while the socket 13 forms the distal portion of the shaft. This could also be achieved with a universal joint or flexible shaft segment. This type of articulation could be locked into place through the use of an outer sleeve 15 or an inner pushshaft 21 that tightens down on the joint in any of these embodiments. These articulations are further disclosed in U.S. Ser. No. 13/163,397, filed Jun. 17, 2011, the specification of which is incorporated by reference in its entirety. The advantage to this configuration could be realized in procedures beyond a TLIF approach (such as in a lateral, PLIF, ALIF, or other anterior or posterior approach, such as posterior cervical, anterior cervical, posterior thoracic, corpectomy, and approaches disclosed in U.S. Ser. No. 13/627,294. filed Sep. 26, 2012, entitled "Method and Devices for a Sub-Splenius/Supra-Levator Scapulae Surgical Access Technique" (Horton et al.,) DEP6642, the specification of which is incorporated by reference in its entirety) in that the instrument is able to angulate in multiple planes and thereby avoid anatomy that may be in the way of a direct approach to the surgical target anatomy. Additionally, the instrument could contain indices that report the selected angle of the instrument tip to the shaft. This allows the user to select predetermined, measured, or favorite angles for their instruments.

The articulating trials and inserters can also provide a means to measure the angulation during articulation. This angle is determined by assessing the difference between the angle following insertion and the angle following articulation. This differential angle is then utilized to ensure the implant is also placed at the identical angle, thereby ensuring trial and implant placement are consistent. Such means are shown in FIGS. 5A-I. In FIGS. 5A-E, the angle can be determined with the use of radiofrequency (RF) triangulation means. Handle 301 contains an RF emitter or reader 303 and three or more passive markers 305 are contained at known locations with the implant/trial(s). Based upon RF tracking of markers, the handle provides a graphic display 307 of trial orientation in both superior/inferior and right/left lateral planes relative to a known reference flat 309 on the handle.

FIGS. 5F-I show the use of angle tracking by measuring movement of cables 351 that provide tensioning. Rotation of a knob 353 located on the handle tensions the cable. The displacement of the cable upon the knob provides for calculation of the angle through a sensor (not shown).

Such angle-measuring features may also be synchronized with image guided surgery assemblies as well.

If less adjustability in the joint is desired or if a means to prevent slip are required, then (now referring to FIG. 6A-D) the ball and socket joint can include flats or facets 19 on the distal and/or proximal aspects of the instrument tip and matching facets on the push shaft, sheath or pull collet that lock the instrument or trial at predetermined angles. Additionally, due to the nature of the flat surfaces and peaks used to create the facets, these geometric features can be used to drive the tip of the instrument to different angles when a tangential force is applied by a member inside the sleeve.

Now therefore, in accordance with the present invention, there is provided a polyaxial articulating trial comprising:

a) a head 31 comprising a distal working tip 33 and a proximal ball 35 comprising i) generally hemispherical portion 37 and ii) a faceted portion, b) a shaft comprising a distal socket and a proximal end 21 attached to a handle, wherein the generally hemispherical portion is pivotally connected to the socket to form a polyaxial joint.

It is contemplated that angular adjustment of the inserter and instrument system can be accomplished either manually or remotely. Passive adjustment involves the surgeon manually adjusting the instrument or trial angle either externally or in-situ to the operative anatomy. For instance, once the instrument/trial is partially inserted, the user can manually loosen the knob and manually adjust the handle of the instrument/trial tip to impact at a different angle. This is achieved by the trial head being pinned to the inner shaft and rotatable around that shaft. The user can either manually lock the trial handle at a new position, and then impact on it without allowing any additional rotation, or leave the handle loose and continue to impact, allowing the trial head to freely turn as it enters the disc space.

Active embodiments of angle adjustment allow for remote angle adjustment or steering. Steering can be accomplished with either a tension cable, a pusher member as is known in the art, or with a belt drive means as is shown in FIGS. 7A-7E. The belt drive embodiment has an internal shaft with a continuous toothed belt 42, much like a conveyer belt or chain saw bar and chain. The proximal end of the instrument has three knobs. One knob 41 drives the belt 42, another 43 changes the plane in which the belt resides by turning it about the long axis of the instrument. The third knob 44 tightens the inner 45 and outer 46 sleeves against the spherical end 47 of the instrument tip, locking its position. The protrusions 48 on the belt interface with mating features 49 on the spherical end of the interchangeable instrument tip 40. Driving the belt causes the instrument tip 40 angle to change in one direction. Changing the angle of the drive belt 42 allows adjustment of the instrument tip angle in a second plane. Through a combination of driving the belt with knob 41 and turning the belt drive with knob 43 around the long axis of the instrument an infinite number of combinations of angles and positions of the instrument tip can be achieved. Once the preferred angle is achieved, this can be locked in place by tightening the inner 45 and outer 46 sleeves against the spherical end 47 of the instrument tip. These tips could be designed to be interchangeable or non-removable.

Now therefore, in accordance with the present invention, there is provided a polyaxial articulating instrument comprising:
   a) an instrument tip 40 comprising a spherical end 47 comprising mating features 49,
   b) a shaft comprising an outer sleeve 46 and an inner sleeve 45 that can compress over the spherical 47 to lock its position,
   c) a belt drive 42 with protrusions 48 contained in the outer and inner sleeves that can be operated with a knob 41 to cause the belt to travel along its track resulting in the protrusions 48 mating with the mating features 49 on spherical end, resulting in an angular movement of the instrument tip,
   d) a mechanism 44 to change the angle of the belt drive with respect to the long axis of the instrument shaft in order to allow angulation of the instrument tip in a different plane,
thereby creating the ability to generate and lock an infinite combination of angles of polyaxial motion of the instrument tip from a proximal end of the instrument.

Figure 8A:
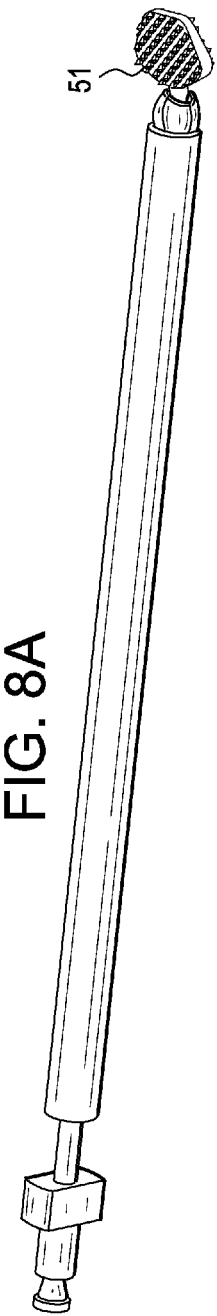
FIGS. 8A-C disclose polyaxial instruments of the present invention having various working tips.
Figure 8B:
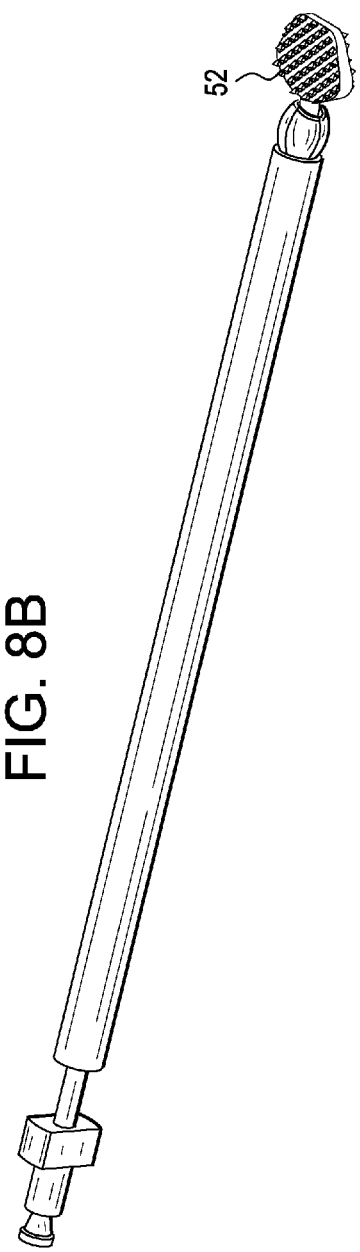
Figure 8C:
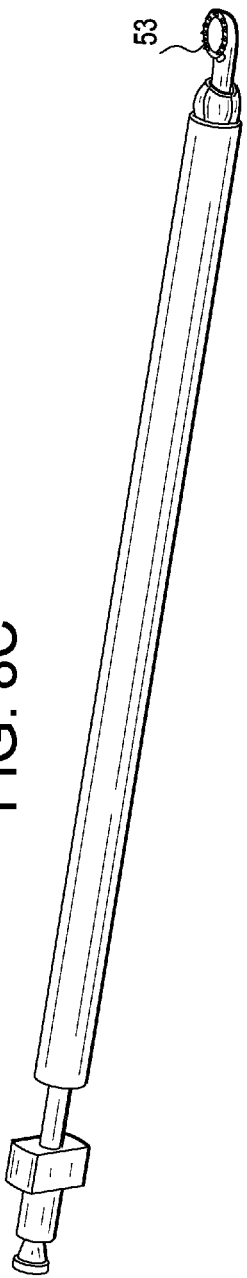

It is contemplated that the articulating trial of the present invention may simply be one embodiment of a more general class of articulating instruments having pivoting instrument tips. These tips could have interchangeable heads so as to provide modularity within a certain type of head (e.g., trials heads of different sizes) and across different types of head (e.g., a trial head and a curette). The instrument handle and shaft of this modular instrument may contain the articulating joint that can articulate in infinite planes, and the different working tips can be rigidly and removeably attached to this handle and shaft. The instrument head generally includes a working tip that allows the instrument to function as an instrument selected from a group comprising a scalpel, a curette, a rasp, a spreader, a shaver, a cobb elevator, a penfield, a woodson, a chisel, an osteotome, a trial, etc. . . . The modular straight rasp 51, angled rasp 52 and straight curette 53 embodiments of these instruments are shown in the images attached as FIGS. 8A-C. The ability to set this modular pivoting instrument to any angle and then lock the angle would allow a smaller number of handles to support a large number of different instruments in a set, and also would allow the surgeon to tailor the angulation of any of their instruments to the exact position they prefer. The benefits of this embodiment could include higher customer satisfaction, better spinal column, discectomy and endplate preparation, and reduced set cost and weight.

Therefore, in accordance with the present invention, there is provided a kit comprising:
   a) a first working head having a distal working tip and a proximal end,
   b) a second working head having a distal working tip and a proximal end,
   c) a shaft having a proximal end having a handle and a distal end,
   wherein the proximal end of each working head and the distal end of the shaft are connectable by a pivoting joint.

Preferably, the first and second working heads are selected from the group consisting of a scalpel, a curette, a rasp, a spreader, a shaver, a cobb elevator, a penfield, a woodson, a chisel and an osteotome, a trial, as well as power tools including aspiration tips, burrs, drills, saw blades, etc. . . . The different working tips can include other devices known to spinal procedure art, i.e., fiber optic lighting, scopes/camera for tissue visualization or radiofrequency devices for tissue ablation and removal.

FIGS. 9A-C disclose one method of using a trial of the present invention. First, the selected modular trial head 201 is inserted into handle 203. Next, the knob 205 is turned to thread-in the trial head. When the trial head is partially threaded-in, the trial head is loose, and handle 203 can be pivoted with respect to the trial head about pivot point 207. As the knob continues to be turned, the trial head is drawn into a bore 209 in the shaft of the handle, and locks into the teeth on the outer surface of the shaft. In this position, the trial head can no longer pivot and its angular position is locked.

In some embodiments of the present invention, the devices of the present invention are used to manipulate tissue in either an intervertebral disc or a vertebral body in the lumbar spine. In some embodiments of the present invention, the devices of the present invention are used to manipulate tissue in either an intervertebral disc or a vertebral body in the cervical spine. In some embodiments of the present invention, the devices of the present invention are used to manipulate tissue in either an intervertebral disc or a vertebral body in the thoracic spine.

The trial head could be made from stainless steel with machined features showing its placement on X-Ray, or alternatively it could be made from a radiolucent material, such as a polymer, and have a combination of radiopaque pins and spheres embedded in it that exactly match the markers in the implant that is being trialed for.

The articulating inserter and instrument system can be sold as prepackaged sterile to allow all instruments and trials for a specific procedure to be provided to the operating room without sterile processing by the hospital staff.

For the purposes of the present invention, the term "polyaxial joint" means a joint that can articulate in multiple planes.

Whereas the above-disclosed assemblies generally form a polyaxial joint using both the implant and inserter components, it is further contemplated that, in some embodiments, the entire polyaxial joint may be provided in just the inserter component.

Therefore, in accordance with the present invention, there is provided a method of preparing an intervertebral disc space or vertebral body in a spinal column in a patient, comprising the step of:
   a) inserting at least a portion of a polyaxial instrument into the intervertebral disc space or the vertebral body, wherein the instrument comprises a distal spinal implant connected to a proximal inserter, wherein the proximal inserter comprises a polyaxial joint.

Preferably, the proximal inserter comprising a polyaxial joint is used during an approach to the spinal column selected from the group consisting of an anterior approach, a posterior approach, a lateral approach, a transforaminal approach and an anterolateral approach.

For example, and now referring to FIGS. 10A-C, in some embodiments, the inserter with a wholly-contained polyaxial joint comprises:
a) a proximal handle (not shown),
b) an intermediate shaft 401, and
c) a distal shaft 403 having a distal attachment feature 405, wherein the polyaxial joint 407 is formed between the intermediate shaft and the distal shaft.

In some embodiments, and now referring to FIG. 10C, the inserter further comprises:
d) a proximal tube 409 disposed about the intermediate shaft, and
e) a distal tube 411 disposed about the distal shaft.

In some embodiments, and now referring to FIG. 10B, the polyaxial joint comprises:
a) the intermediate shaft 401 having a distal end portion 423 forming two axially extending flanges 425, each flange having a through-hole 427,
b) the distal shaft 403 having a proximal end portion 433 forming two axially extending flanges 435, each flange having a through-hole 437, and
c) a substantially spherical body 439 having four rods 443, 445 extending therefrom, wherein a first two rods are received in the throughholes of the flanges of the intermediate shaft, and
wherein a second two rods are received in the throughholes of the flanges of the distal shaft.

In some embodiments, each rod is either coaxial with or perpendicular to the other rods.

Preferably, a first pair of co-axial rods 443 are received in the throughholes of the flanges of the intermediate shaft, and a second pair 445 of co-axial rods are received in the throughholes of the flanges of the distal shaft.

In other embodiments, the polyaxial joint can be of a ball-and-socket type, comprising a portion of a ball formed in an end of one of the shafts and a portion of the socket formed in an opposing end of the other of the shafts.

In some embodiments, and now referring to FIGS. 10D-H, the polyaxial joint 451 comprises:
a) the intermediate shaft 453 having a distal end portion 455 having a recess 457 therein, wherein the recess comprises a first plurality of grooves 459,
b) the distal shaft 463 having a proximal end portion 465 forming a projection 467, wherein the projection comprises a second plurality of grooves 469, and
c) a plurality of bearings 471, wherein the projection is received in the recess so that the first plurality of grooves align with the second plurality of grooves, and
wherein the plurality of bearings are respectively received between the aligned grooves.

In some embodiments, control of the pivoting movement of the inserter joint can be achieved by manipulating steering wires. Now referring to FIGS. 11A-C, in some embodiments, the inserter (with a wholly contained polyaxial joint) comprises:
a) a proximal handle (not shown),
b) an intermediate shaft (not shown), and
c) a distal shaft having a distal attachment feature 485 and d) a distal tube 487 surrounding the distal shaft, wherein the tube has at least two steering wires 489 attached thereto, wherein a pivoting joint 490 is formed between the intermediate shaft and the distal shaft.

Figure 11A:
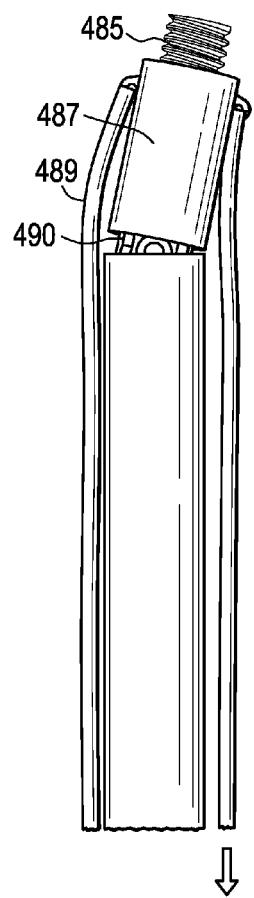
FIGS. 11A-C disclose a polyaxial inserter with steering wires.
Figure 11B:
Figure 11C:

FIG. 11A shows the inserter when there is no tension on either steering wire. FIG. 11B shows how tensioning the lower wire has the effect of moving the distal tube/shaft in the lower direction. FIG. 11C shows how tensioning the upper wire has the effect of moving the distal tube/shaft in the higher direction.

In some embodiments thereof, the distal tube has two steering wires attached thereto (as shown in FIGS. 11A-C). The steering wires are attached to the distal tube at locations that are diametrically opposed. In this embodiment, pivoting movement of the joint may be restricted to a single plane.

In other embodiments thereof (not shown), the distal tube has four steering wires attached thereto. The four steering wires are attached to the distal shaft at locations that are separated by 90 degrees. In this embodiment, pivoting movement of the joint is provided in 3-dimensional space.

In other embodiments, the distal tube can be removed and the steering wires can be attached directly to the distal shaft.

In other embodiments, the distal attachment feature 492 can comprise a pair of flexible arms 491, as shown in FIGS. 12A-F. These arms typically removably mate with a pair of recesses located on the proximal end portion of the implant. Alternatively, the feature can be inserted through a hole in the proximal portion of the implant, and the arms can mate with the inner wall of the implant.

Figure 12A:
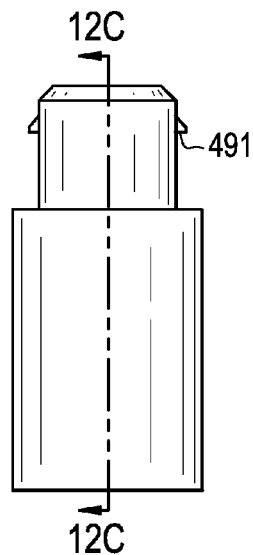
FIGS. 12A-F disclose a portion of an inserter with flexible arms as an attachment feature.
Figure 12B:
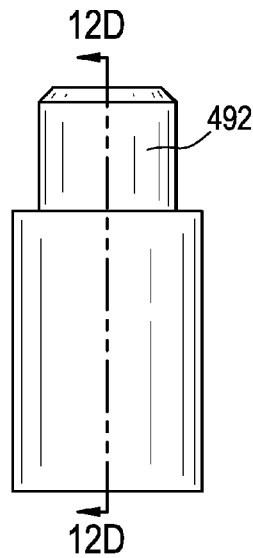
Figure 12C:
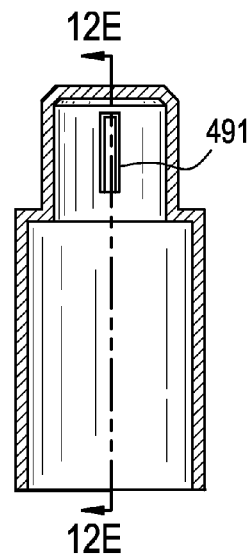
Figure 12D:
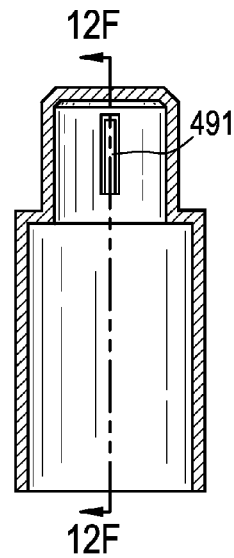
Figure 12E:
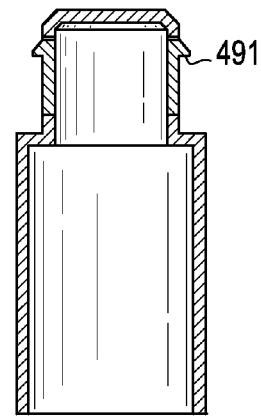
Figure 12F:
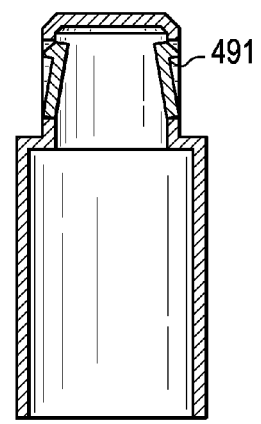
Figure 12G:
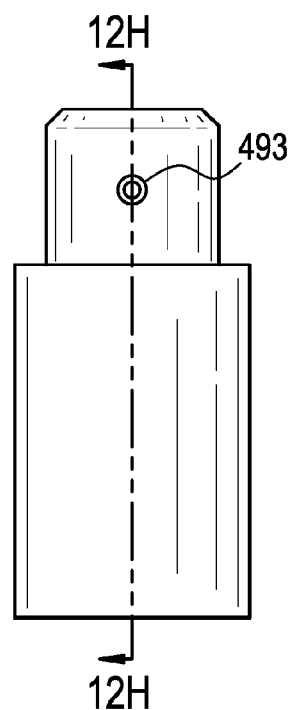
FIGS. 12G-H disclose a portion of an inserter with a ball plunger as an attachment feature.
Figure 12H:
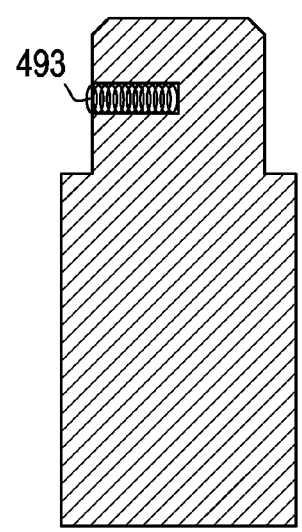

In other embodiments, the distal attachment feature can comprise a ball plunger 493, as shown in FIGS. 12G-H. This ball plunger typically removably mates with a pocket located on the proximal end portion of the implant. Alternatively, the feature can be inserted through a hole in the proximal portion of the implant, and the ball plunger can mate with the inner wall of the implant.

In some embodiments, the mating features on the tips of FIGS. 12A-F and 12G-H and the mating implants can be reversed. For example, the ball plunger feature may be placed on the implant.

Figure 12I:
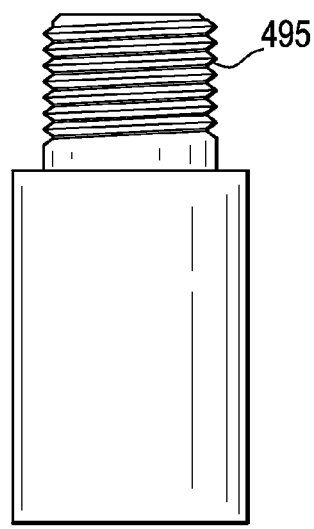
FIG. 12I disclose a portion of an inserter with a thread as an attachment feature.

In some embodiments, the distal attachment feature can comprise a thread 495. Such a feature is shown in FIG. 12I. This thread typically removably mates with a threaded receiver located on the proximal end portion of the implant.

Pivotal movement of the polyaxial joint in the inserters of the present invention is carried out by manipulating the proximal and distal tube components. In particular, when the knob of the handle is manipulated to retract the distal tube, the distal tube contacts the proximal tube, thereby locking the articulation produced by the shaft components within the tubes. When knob manipulation causes the distal tube to be advanced forward, the distal tube releases contact with the proximal tube, thereby unlocking the locked articulation produced by the shaft components therein.

Figure 13A:
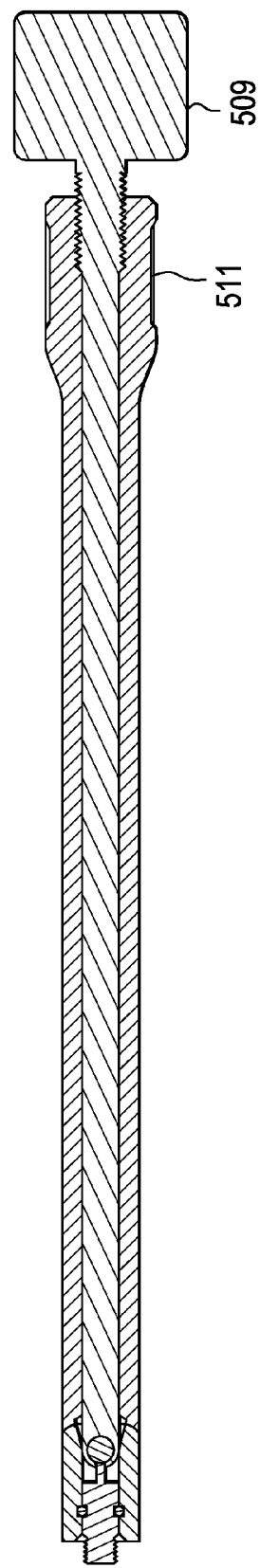
FIG. 13A discloses an embodiment of the polyaxial inserter.
Figure 13B:
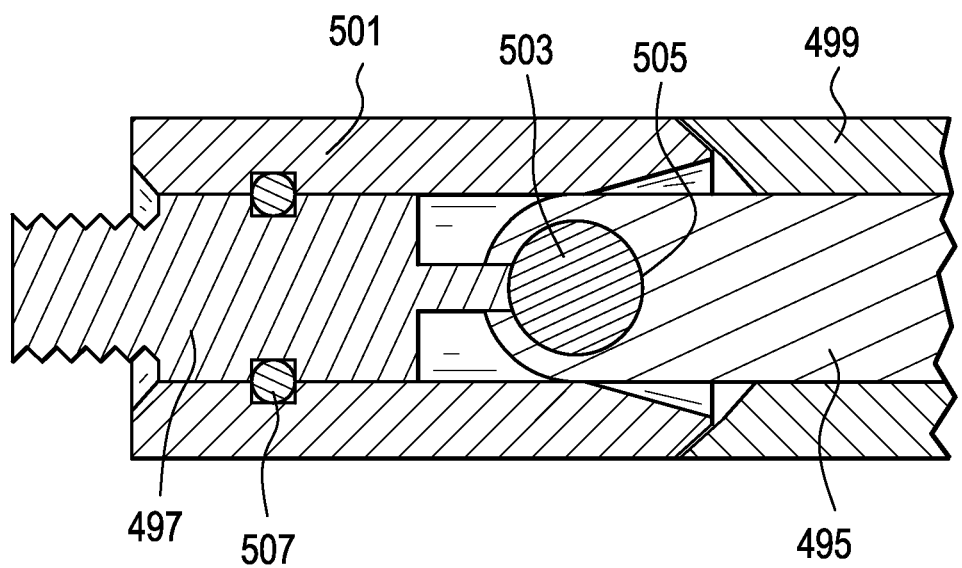
FIG. 13B shows an enlarged view of the polyaxial mechanism of FIG. 13A.

The mechanics of the angle adjustment mechanism just described is shown in FIG. 13A-B. Proximal shaft 495 and distal shaft 497 are respectively shown disposed inside of proximal tube 499 and distal tube 501. Also, extending from distal shaft 501 is a spherical component 503. This spherical component is received in a socket 505 formed in the distal end of the proximal shaft to form a polyaxial joint. Interposition of O-ring 507 causes the distal tube to be axially fixed about the distal shaft, while the proximal tube is slidable with respect to the proximal shaft. Accordingly, the two shafts and the distal tube move as one.

Accordingly, when the knob 509 of the handle 511 is manipulated by the surgeon to retract the proximal shaft, the distal tube also retracts to contact the proximal tube, thereby locking the articulation produced by the shaft components within the tubes. When knob manipulation causes the proximal shaft to advance, the distal tube is also advanced forward. This releases its contact with the proximal tube, thereby unlocking the articulation produced by the shaft components therein.

Figure 13C:
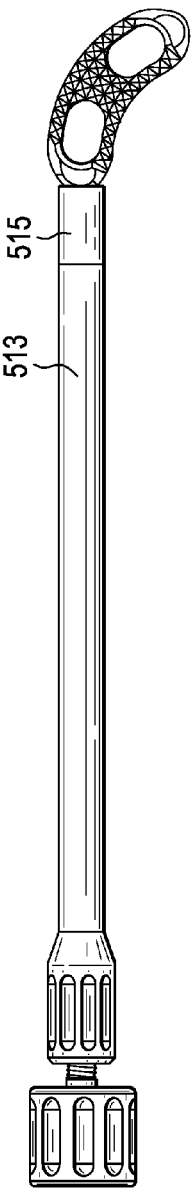
FIGS. 13C-F disclose a polyaxial inserter-implant assembly having different angles of orientation.

In some embodiments, the assembly of the present invention is provided with an initial angle between the inserter and the implant, as shown in FIG. 13C, wherein the proximal 513 and distal 515 tubes are brought together and the underlying articulation is locked at a first angle. This first angle is selected to provide an orientation that is near in-line as possible. (As an alternative example, the orientation may also be that of FIG. 14A). The surgeon then inserts the assembly into the disc space, with the inserter locked at this first angle.

Figure 13D:
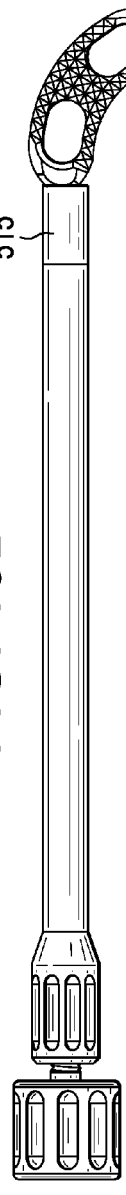

After insertion, and now referring to FIG. 13D, the surgeon manipulates the knob to advance the distal tube 515. This loosens the overall sleeve and thereby unlocks the underlying articulation.

Figure 13E:

Next, and now referring to FIG. 13E, with the articulation unlocked, the surgeon pivots the proximal tube 513 to adjust the angle of the articulation to a second angle. This second angle is selected to reduce invasiveness and facilitate insertion.

Figure 13F:
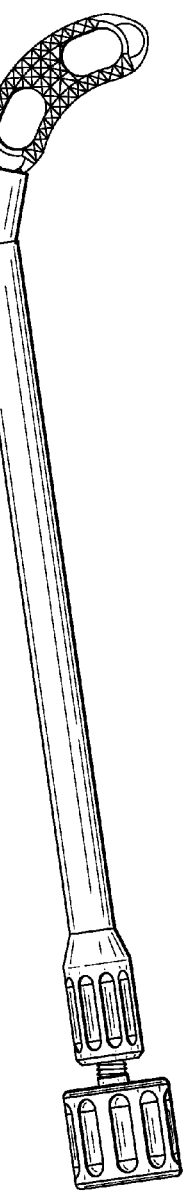

Next, and now referring to FIG. 13F, with the articulation now set at the new angle, the knob is again manipulated to pull the distal tube 515 backwards, thereby tightening the overall sleeve, and re-locking the articulation at the second angle. The surgeon is now ready to rotate the cage.

These angle adjustment steps can be re-performed until the desired positioning and orientation of the implant is achieved.

Using the adjustment mechanism shown in FIGS. 13C-F, the surgeon can continually re-adjust the angle of the implant vis-á-vis the inserter during insertion. A plurality of such positions are shown in FIGS. 14 A-D. FIG. 14A shows the initial orientation of the implant 519 during insertion. FIG. 14B shows an intermediate orientation of the implant 519. FIG. 14C shows a final orientation of the implant 519. FIG. 14D shows the range of orientations of FIGS. 14A-C.

FIGS. 15 A-C provide perspective views of the orientations of the implant 519 disclosed in FIGS. 14A-C.

Now referring to FIGS. 16A-C, there are provided exploded and assembled views of the assembly of the present invention, comprising:

a) an inserter having a wholly-contained polyaxial joint 523, comprising:
 i) a proximal handle (not shown),
 ii) an intermediate shaft 525 having a distal socket 527, and
 iii) a distal shaft 529 having a proximal socket 531 and a distal thread attachment feature (not shown),
 iv) a bearing 533 received in both sockets,
b) a spinal implant 535 comprising a threaded attachment feature 537,
 wherein the attachment feature of the inserter is received in the attachment feature of the spinal implant.

In some embodiments, the socket of each shaft comprises a pair of arced extensions 539, 541 extending axially from the shaft, the bearing is a substantially spherical body 543 having a pair of grooves 545 therein, and the grooves contact the arced extensions. Preferably, the grooves are disposed about 90 degrees from each other.

FIG. 16 D discloses the assembly of FIG. 16A, with proximal 549 and distal 550 tubes added to the inserter to surround the proximal and distal shafts. In addition, the threaded attachment feature 551 of the inserter is shown as received in the threaded attachment feature 537 of the spinal implant.

Figure 16E:
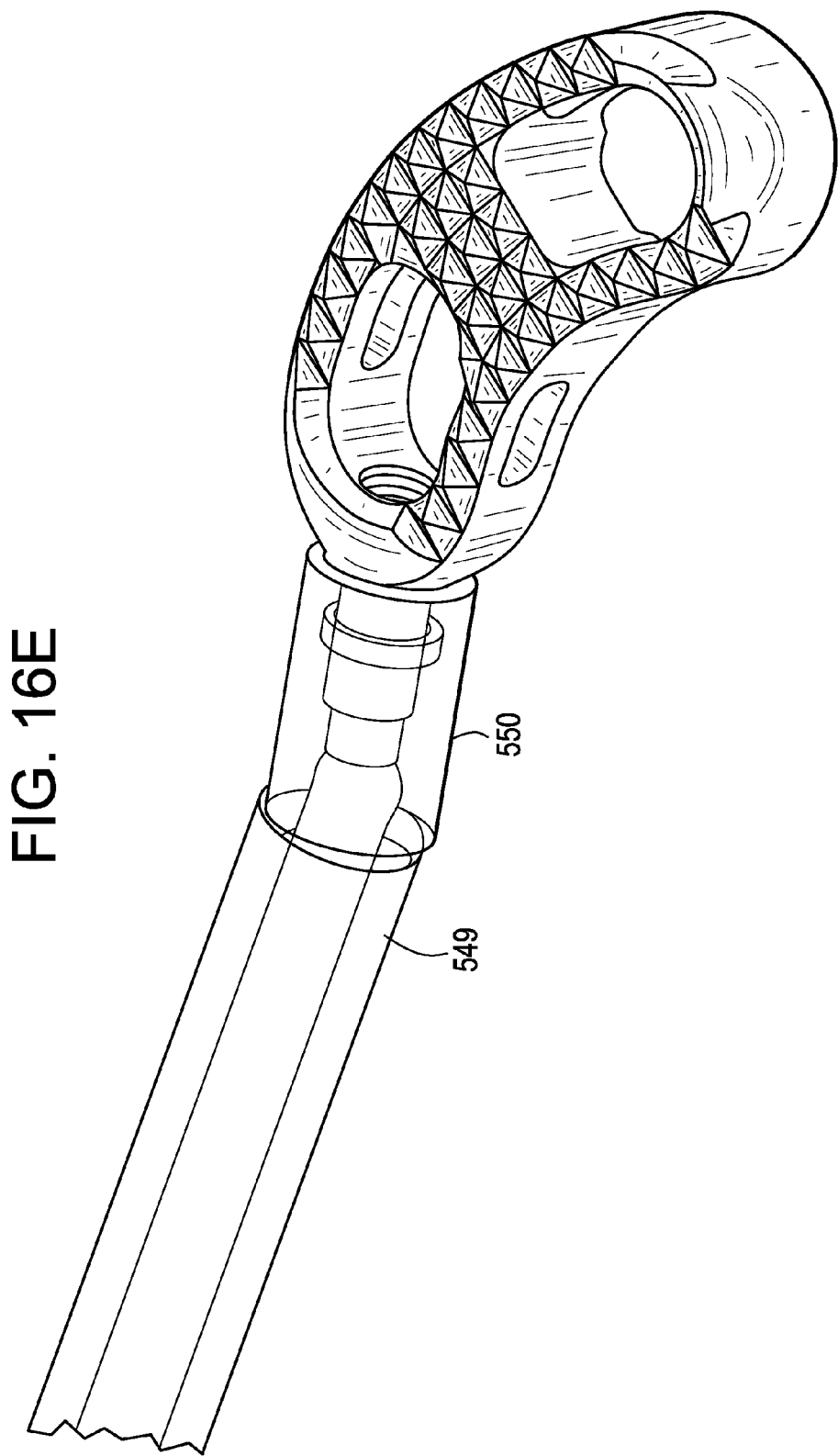

FIG. 16E also discloses the assembly of FIG. 16A, with proximal 549 and distal 550 tubes added to the inserter to surround the proximal and distal shafts.

We claim:

1. A method of preparing an intervertebral disc space or vertebral body in a spinal column in a patient, comprising the steps of:
 a) inserting a polyaxial instrument into the intervertebral disc space or the vertebral body via an approach selected from the group consisting of an anterior approach, a posterior approach, a transforaminal approach and an anterolateral approach to the spinal column, wherein the instrument comprises a distal head and a proximal shaft connected by a polyaxial joint, whereby the polyaxial joint allows the distal head to polyaxially pivot about the proximal shaft, and wherein the distal head is a trial adapted to assess implant fit in the disc space,
 b) determining an angle set by the head and shaft in the disc space via a graphic display of trial orientation on the instrument, wherein the graphical display reports the angle as a polyaxial insertion angle of the head relative to the shaft,
 c) removing the distal head of the instrument from the disc space
 d) fixing the angle to an apparatus comprising an implant attached to an inserter, and
 e) inserting the implant into the disc space via the approach, wherein the implant-inserter apparatus is fixed at the angle.

2. The method of claim 1 wherein the distal head comprises a distal working tip and a proximal generally hemispherical portion, the proximal shaft comprises a distal socket, and wherein the polyaxial joint comprises the generally hemispherical portion received in the socket.

3. The method of claim 2 wherein the socket has a collet that is compressed upon retraction into a sheath and thereby grips the generally hemispherical portion to lock an orientation of the instrument.

4. The method of claim 2 further comprising, after step b), the step of:
 f) loosening the joint and adjusting the shaft to a second angle.

5. The method of claim 4 wherein the step of loosening the joint includes turning a knob on the shaft.

6. The method of claim 5 further comprising the step of:
 g) leaving the joint loose while impacting on the shaft, thereby allowing the distal head to freely turn as it enters the disc space.

7. The method of claim 4 further comprising the step of:
 g) locking the loosened joint at the second angle, and then impacting on the shaft without allowing any additional rotation.

8. The method of claim 4 wherein the adjustment is accomplished manually.

9. The method of claim 4 wherein the adjustment is accomplished remotely.

10. A method of preparing an intervertebral disc space or a vertebral body in a spinal column in a patient, comprising the steps of:
- selecting an articulating instrument comprising a distal head and a proximal shaft connected by an articulating joint, whereby the articulating joint is adapted to allow the distal head to polyaxially pivot about the proximal shaft, and wherein the distal head is a trial adapted to assess implant fit in the disc space,
- partially inserting the articulating instrument into the intervertebral disc space or vertebral body, wherein the articulating joint is held locked at an angle of the head relative to the shaft,
- loosening the joint,
- determining an angle set by the head and shaft in the disc space via a graphic display of trial orientation on the instrument, wherein the graphical display reports the angle as a polyaxial insertion angle of the head relative to the shaft,
- adjusting the shaft of the instrument to a different angle,
- locking the shaft at the different angle, and then
- impacting on the shaft without allowing any additional rotation, and
- removing the distal head of the instrument from the disc space.

11. The method of claim 10 further comprising the step of: once the instrument is fully inserted, loosening the joint.

12. The method of claim 11, wherein a handle is connected to a proximal end of the shaft, further comprising the steps of:
- removing the handle, and
- rotating the shaft.

13. The method of claim 11 further comprising the step of: reconnecting the handle.

14. The method of claim 13 further comprising the step of: removing the distal head from the disc space with the joint loosened.

15. The method of claim 10 wherein the articulating instrument has a polyaxial joint.

16. The method of claim 15 wherein the polyaxial joint is locked into place through the use of either i) an outer sleeve surrounding the hemispherical portion, wherein the outer sleeve tightens down on the joint or ii) an inner push shaft located within the sleeve that tightens down on the joint.

17. The method of claim 15 wherein the shaft is adjusted to a different angle manually or remotely.

18. The method of claim 10 wherein the instrument is partially inserted via an approach selected from the group consisting of an anterior approach, a posterior approach, a transforaminal approach and an anterolateral approach.

19. The method of claim 10 further comprising the steps of:
- fixing the different angle to an apparatus comprising an implant attached to an inserter having a shaft, and
- inserting the implant into the disc space via the approach, wherein the implant-inserter apparatus is fixed at the angle.

20. A method of preparing an intervertebral disc space in a patient, comprising the steps of:
- selecting an articulating instrument comprising a distal head and a proximal shaft connected by an articulating joint, whereby the articulating joint is adapted to allow the distal head to polyaxially pivot about the proximal shaft, and wherein the distal head is a trial adapted to assess implant fit in the disc space,
- partially inserting the polyaxial instrument into the intervertebral disc space,
- wherein the articulating joint is held locked at a first angle, the proximal shaft having a proximal end connected to a handle,
- loosening the joint,
- adjusting the shaft of the instrument to a second angle,
- leaving the joint loose while impacting the shaft, thereby allowing the distal head to freely turn as it enters the disc space,
- determining an angle set by the head and shaft in the disc space via a graphic display of trial orientation on the instrument, wherein the graphical display reports the angle as a polyaxial insertion angle of the head relative to the shaft,
- and
- removing the distal head of the instrument from the disc space.

21. The method of claim 20 further comprising the step of: removing the handle after loosening the joint.

22. The method of claim 21 further comprising the step of: adjusting the shaft to a third angle.

23. The method of claim 21 further comprising the step of: reconnecting the handle.

24. The method of claim 20 wherein the joint is a polyaxial joint.

25. The method of claim 24 wherein the polyaxial joint is locked into place through the use of either i) an outer sleeve surrounding the hemisphere that tightens down on the joint or ii) an inner pushshaft located in the sleeve that tightens down on the joint.

26. The method of claim 24 wherein the shaft is adjusted to a second angle manually or remotely.

27. The method of claim 20 wherein the instrument is partially inserted via an approach selected from the group consisting of an anterior approach, a posterior approach, a transforaminal approach and an anterolateral approach.

28. The method of claim 20 further comprising the steps of:
- fixing the angle to an apparatus comprising an implant attached to an inserter, and
- inserting the implant into the disc space via the approach, wherein the implant-inserter apparatus is fixed at the angle.

29. A method of preparing a spinal column in a patient, comprising the steps of:
- selecting an articulating instrument comprising a distal head and a proximal shaft connected by an articulating joint, whereby the articulating joint is adapted to allow the distal head to polyaxially pivot about the proximal shaft, and wherein the distal head is a trial adapted to assess implant fit in the disc space,
- inserting the articulating instrument into the spinal column, wherein the articulating joint is held locked at an angle, the proximal shaft having a proximal end connected to a handle,
- determining an angle set by the head and shaft in the disc space via a graphic display of trial orientation on the instrument, wherein the graphical display reports the angle as a polyaxial insertion angle of the head relative to the shaft,
- removing the handle from the shaft while the head is partially in the spinal column,
- reconnecting the handle while the head is partially in the spinal column, and
- removing the distal head of the instrument from the disc space.

30. The method of claim 29 further comprising the step of:
taking an x-ray of the spinal column between steps b) and c).

31. The method of claim 29 further comprising the step of:
rotating the shaft to produce a different angle at the joint between steps b) and c).

32. The method of claim 31 further comprising the step of:
performing a discectomy posterior to the distal head.

33. The method of claim 29 further comprising the step of:
removing the instrument from the spinal column with the joint loosened.

34. A method of preparing the spinal column of a patient, comprising the steps of:
selecting an articulating instrument comprising a distal head and a proximal shaft connected by an articulating joint, whereby the articulating joint is adapted to allow the distal head to polyaxially pivot about the proximal shaft, and wherein the distal head is a trial adapted to assess implant fit in the disc space,
partially inserting the articulating instrument into the column, wherein the articulating joint is held locked at an angle,
loosening the instrument joint,
determining an angle set by the head and shaft in the disc space via a graphic display of trial orientation on the instrument, wherein the graphical display reports the angle as a polyaxial insertion angle of the head relative to the shaft,
adjusting the shaft of the instrument to a different angle,
locking the shaft at the different angle, and then
impacting on the shaft without allowing any additional rotation, and
removing the distal head of the instrument from the disc space.

35. A method of preparing an intervertebral disc space or vertebral body in a spinal column in a patient, comprising the step of:
a) inserting at least a portion of an articulating instrument into the intervertebral disc space or the vertebral body, wherein the instrument comprises a distal spinal implant connected to a proximal inserter, wherein the proximal inserter comprises a distal head and a proximal shaft connected by an articulating joint, whereby the articulating joint is adapted to allow the distal head to polyaxially pivot about the proximal shaft, and wherein the distal head is a trial adapted to assess implant fit in the disc space,
b) determining an angle set by the head and shaft in the disc space via a graphic display of trial orientation on the instrument, wherein the graphical display reports the angle as a polyaxial insertion angle of the head relative to the shaft,
and
c) removing the distal head of the instrument from the disc space.

36. The method of claim 35 wherein the proximal inserter comprising the polyaxial joint is used during an approach to the spinal column selected from the group consisting of an anterior approach, a posterior approach, a lateral approach, a transforaminal approach and an anterolateral approach.

37. The method of claim 35 wherein the insertion is carried out with the inserter having a locked polyaxial joint having a first angle.

38. The method of claim 37 further comprising the step of:
c) unlocking the joint while the implant is in the spinal column.

39. The method of claim 38 further comprising the step of:
d) adjusting the first angle of the unlocked joint to a second angle.

40. The method of claim 39 further comprising the step of:
e) locking the joint at the second angle.

41. The method of claim 40 further comprising the step of:
e) manipulating the inserter within the spinal column with the joint at the second angle.

42. The method of claim 35 wherein the joint is a ball-and-socket joint.

43. The method of claim 35 wherein the joint is a three-piece joint.

44. The method of claim 43 wherein the three-piece joint comprises a substantially spherical body.

* * * * *